US012221475B2

United States Patent
Hu et al.

(10) Patent No.: US 12,221,475 B2
(45) Date of Patent: Feb. 11, 2025

(54) CHIMERIC ANTIGEN RECEPTOR AND APPLICATION THEREOF

(71) Applicant: CAS Lamvac (Guangzhou) Biomedical Technology Co., Ltd., Guangzhou (CN)

(72) Inventors: Wen Hu, Guangdong (CN); Yongchao Yao, Guangdong (CN); Wenzhong Guo, Guangdong (CN); Yinbo Jiang, Guangdong (CN); Shuozhou Huang, Guangdong (CN); Ting Jiang, Guangdong (CN); Jiaojiao Li, Guangdong (CN); Zhu Tao, Guangdong (CN); Yanli Gu, Guangdong (CN); Huihui Zhang, Guangdong (CN); Li Qin, Guangdong (CN); Xiaoping Chen, Guangdong (CN)

(73) Assignee: CAS Lamvac (Guangzhou) Biomedical Technology Co., Ltd., Guangzhou (CN)

( * ) Notice: Subject to any disclaimer, the term of this patent is extended or adjusted under 35 U.S.C. 154(b) by 1294 days.

(21) Appl. No.: 17/051,747

(22) PCT Filed: Nov. 29, 2017

(86) PCT No.: PCT/CN2017/113661
§ 371 (c)(1),
(2) Date: Oct. 29, 2020

(87) PCT Pub. No.: WO2019/104562
PCT Pub. Date: Jun. 6, 2019

(65) Prior Publication Data
US 2021/0221880 A1  Jul. 22, 2021

(51) Int. Cl.
| | |
|---|---|
| C07K 16/20 | (2006.01) |
| A61K 38/00 | (2006.01) |
| A61K 39/00 | (2006.01) |
| A61P 35/00 | (2006.01) |
| C07K 14/705 | (2006.01) |
| C07K 14/725 | (2006.01) |
| C12N 5/0783 | (2010.01) |

(52) U.S. Cl.
CPC ............ *C07K 16/205* (2013.01); *A61K 39/00* (2013.01); *A61K 39/0011* (2013.01); *A61K 39/4611* (2023.05); *A61K 39/4631* (2023.05); *A61K 39/4647* (2023.05); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *A61K 38/00* (2013.01); *A61K 2239/13* (2023.05); *A61K 2239/24* (2023.05); *C07K 2317/565* (2013.01); *C07K 2317/622* (2013.01); *C07K 2317/76* (2013.01); *C07K 2319/02* (2013.01); *C07K 2319/03* (2013.01); *C07K 2319/22* (2013.01); *C07K 2319/30* (2013.01); *C07K 2319/33* (2013.01); *C07K 2319/43* (2013.01)

(58) Field of Classification Search
CPC .............. C07K 16/205; C07K 14/7051; C07K 14/70517; C07K 14/70521; C07K 14/70578; C07K 2317/565; C07K 2317/622; C07K 2317/76; C07K 2319/02; C07K 2319/03; C07K 2319/22; C07K 2319/30; C07K 2319/33; C07K 2319/43; A61K 35/17; A61K 38/00; A61K 2039/5156; A61K 2039/5158
See application file for complete search history.

(56) References Cited

U.S. PATENT DOCUMENTS

| | | |
|---|---|---|
| 9,233,125 B2 | 1/2016 | Davila et al. |
| 9,926,350 B2 | 3/2018 | Salanti et al. |

FOREIGN PATENT DOCUMENTS

| | | |
|---|---|---|
| CN | 102775500 | 11/2012 |
| CN | 104126009 | 10/2014 |
| CN | 105753991 A | 7/2016 |
| CN | 106977607 A | 7/2017 |
| WO | 2012082841 A2 | 6/2012 |
| WO | 2013117705 A1 | 8/2013 |
| WO | 2015095952 | 7/2015 |

(Continued)

OTHER PUBLICATIONS

Office Action received in corresponding Chinese Application No. 201780001820. 4 mailed Jul. 31, 2020.
Clausen et al., "Oncofetal Chondroitin Sulfate Glycosaminoglycans Are Key Players in Integrin Signaling and Tumor Cell Motility", Published OnlineFirst Sep. 21, 2016; DOI: 10.1158/1541-7786. MCR-16-0103.
Rodgers et al., "Switch-mediated activation and retargeting of CAR-T cells for B-cell malignancies", PNAS | Published online Jan. 12, 2016 | E459-E468.
Salanti et al., "Targeting Human Cancer by a Glycosaminoglycan Binding Malaria Protein", Cancer Cell 28, 500-514, Oct. 12, 2015 ª2015 Elsevier Inc.

(Continued)

*Primary Examiner* — Mark Halvorson
*Assistant Examiner* — Dennis J Sullivan
(74) *Attorney, Agent, or Firm* — Wood, Phillips, Katz, Clark & Mortimer

(57) ABSTRACT

Provided are a chimeric antigen receptor and an application thereof; said chimeric antigen receptor contains a domain which identifies any one of, or a combination of at least two of, the malarial protein VAR2CSA, a protein tag on malarial protein VAR2CSA, or a compound capable of labeling the malarial protein VAR2CSA. The chimeric antigen receptor can identify the VAR2CSA protein or the recombinant protein (rVAR2) of any one of, or at least two of, the domains of the VAR2CSA protein which can bind to placental-like chondroitin sulfate A (pl-CSA). The VAR2CSA protein or rVAS2 protein is capable of targeting several different types of tumor cells by means of binding to the pl-CSA on the surface of the tumor cell.

8 Claims, 14 Drawing Sheets
Specification includes a Sequence Listing.

(56) References Cited

FOREIGN PATENT DOCUMENTS

| WO | 2016135291 A1 | 9/2016 |
|----|---------------|--------|
| WO | 2017179015 A1 | 10/2017 |

OTHER PUBLICATIONS

Seiler et al., "An Oncofetal Glycosaminoglycan Modification Provides Therapeutic Access to Cisplatin-resistant Bladder Cancer", Therapeutic Access to Cisplatin-resistant Bladder Cancer. Eur Urol (2017), http://dx.doi.org/10.1016/i.eururo.2017.03.021.

Office Action received in corresponding Great Britain Application No. GB2015416.7 mailed Feb. 1, 2022.

European International Search Report for corresponding European Application No. 17933216.8 mailed Nov. 15, 2021.

Joergensen et al., "The kinetics of antibody binding to Plasmodium falciparum VAR2CSA PfEMP1 antigen and modelling of PfEMP1 antigen packing on the membrane knobs", Malaria Journal 2010, 9:100.

Lohmueller et al., "mSA2 affinity-enhanced biotin-binding CART cells for universal tumor targeting", Oncoimmunology, 2018, vol. 7, No. 1, e1368604 (6 pages) https://doi.mg/10.1080/2162402X.2017.1368604.

International Search Report for corresponding PCT Application No. PCT/CN2017/113661 mailed Sep. 4, 2018.

Cao. Y. et al. "Design of Switchable Chimeric Antigen Receptor T Cells Targeting Breast Cancer" Angewandte Chemie—International Edition, vol. 55, No. (26), Jun. 20, 2016 (Jun. 20, 2016), ISSN: 1521-3773, pp. 7520-7524, see abstract, and figure 1.

Dilution factor of murine polyclonal
antibody against rVAR2 protein

Figure 2

CHIMERIC ANTIGEN RECEPTOR AND APPLICATION THEREOF

TECHNICAL FIELD

The present invention relates to the field of cellular immunotherapy of tumors and, in particular, to a chimeric antigen receptor and a use thereof, especially a chimeric antigen receptor using malarial protein VAR2CSA or the recombinant protein (rVAR2) of any one or at least two domains in the VAR2CSA protein that can bind to the placental-like chondroitin sulfate A as a navigation system and a use thereof for treating tumors.

BACKGROUND

Cancer is the second largest lethal disease after cardiovascular disease in the world. About 8.8 million people died of cancer worldwide only in 2015 (GBD 2015 Mortality and Causes of Death Collaborators, *Lancet*. 2016, 388 (10053): 1459-1544). Immunotherapy is considered to be the fourth cancer treatment after surgery, radiotherapy and chemotherapy. Chimeric Antigen Receptor (CAR) T-Cell Immunotherapy (CAR-T) is the most popular and most successful cellular immunotherapy in recent years and is a huge success in the treatment of B-cell acute lymphoblastic leukemia and B-cell lymphoma (Porter et al., *N Engl J Med*. 2011, 365(8): 725-33; Grupp et al., *N Engl J Med*. 2013, 368(16): 1509-18; Gill et al., *Blood Rev*. 2016, 30(3): 157-67). The potential of the CAR-T for treating solid tumors is being tapped (Newick et al., *Annu Rev Med*. 2017, 68:139-152).

Compared with tumor vaccines with a low objective response rate in clinical trials, the cellular immunotherapy is more expected (Rosenberg et al., *Nat Med*. 2004, 10(9): 909-15). Different from traditional adoptive cellular immunotherapy (such as the isolation and in vitro amplification of tumor infiltrating T lymphocytes (TILs) for reinfusion (Rosenberg and Restifo, *Science*. 2015, 348(6230): 62-8), DC-CIK therapy (Mesiano et al., *Expert Opin Biol Ther*. 2012, 12(6): 673-84) and engineered T cell antigen receptor T cell (TCR-T) therapy (Klebanoff et al., *Nat Med*. 2016, 22(1): 26-36)), the CAR-T technology can recombine CAR molecules into CD3$^+$ T cells, and the binding to target cells does not depend on the mediation of MHC molecules, avoiding many intermediate links for immune cells to eliminate cancer cells in the natural state, and enabling CAR-T cells to accurately identify antigens of cancer cells and directly target and kill cancer cells (Fesnak et al., *Nat Rev Cancer*. 2016, 16(9): 566-81; Lim and June, *Cell*. 2017, 168(4): 724-740). With respect to immune checkpoint blockers represented by antibodies specific to CTLA-4 and PD-1/PD-L1 (Pauken et al., *Science*. 2016, 354(6316): 1160-1165), CAR-T cells can proliferate and maintain their anti-tumor activity in cancer patients. In theory, the CAR-T can effect longer than the treatment with the immune checkpoint blockers.

At present, the international researches on the optimization of CAR-T cells mainly focus on the following aspects (Fesnak et al., *Nat Rev Cancer*. 2016, 16(9): 566-81): (1) specific solid tumor-associated surface antigens are discovered, so as to avoid the off-target effect of CAR-T cells; (2) the targeting of T cells redirected in solid tumors, such as the application of T cells redirected for universal cytokine killing (TRUCKs); (3) the gene editing and cell transfection technologies of CAR-T cells are optimized (Eyquem et al., 2017); (4) the tumor-homing ability of CAR-T cells is improved; (5) the immunosuppression of a tumor microenvironment and the immune escape of tumor cells are avoided; (6) the clinical application safety of the CAR-T is improved, such as the integration of "suicide genes" (Jensen et al., *Biol Blood Marrow Transplant*. 2010, 16(9): 1245-56; Gargett and Brown, *Front. Pharmacol*. 2014, 5(235): 1-7) or "molecular switches" (Rodgers et al., *Proc Natl Acad Sci USA*. 2016, 113(4): E459-68; Wu et al., *Science*. 2015, 350(6258): aab4077; Morsut et al., *Cell*. 2016, 164(4): 780-91), and knocking out endogenous TCRs to prevent graft versus host diseases (GvHDs) (Galetto et al., *Blood*, 2014, 124(21): 1116).

VAR2CSA is a multi-domain protein expressed on the surface of *Plasmodium falciparum*-infected human erythrocytes, and is a member of the *Plasmodium falciparum* erythrocyte membrane protein 1 (PfEMP1) family (such as PlasmoDB: PF3D7_1200600). VAR2CSA can targeted and bind to proteoglycan modified by a placental-like chondroitin sulfate (CS) glycosaminoglycan (GAG) chain (also known as placenta-like chondroitin sulfate A, abbreviated as pl-CSA) to mediate the adhesion of erythrocytes infected with *Plasmodium* to the extracellular matrix and cellular plasma membrane of the placental syncytiotrophoblast layer (Salanti et al., *Mol Microbiol*. 2003, 49(1): 179-91; Salanti et al., *J Exp Med*. 2004, 200(9): 1197-203), which causes *Plasmodium* to infect the placenta of a pregnant woman. It is clinically referred to as placental malaria which can cause abortion and stillbirth. Studies have shown that tumor tissues and placental tissues express similar types of chondroitin sulfate. VAR2CSA can specifically target multiple different types of tumor tissues and cells rather than normal tissues and cells through the interaction with pl-CSA (Salanti et al., *Cancer Cell*. 2015, 28(4): 500-14).

*Plasmodium falciparum* and humans have co-evolved for at least several million years (Rich and Ayala, In Krishna R. Dronamraju, Paolo Arese (Ed). *Emerging Infectious Diseases of the 21st Century: Malaria—Genetic and Evolutionary Aspects*. Springer US 2006. pp. 125-146). The life cycle of the human *Plasmodium falciparum* mainly includes three phases: the sexual stage (occurring within the mosquito vector), liver hepatocytes (pre-erythrocytic stage), and the blood stage (erythrocytic stage) (Bousema et al., *Nat Rev Microbiol*. 2014, 12(12): 833-40). During the co-evolution, human erythrocytes are host cells of the human *Plasmodium falciparum* in the erythrocytic phase. The immune escape of the *Plasmodium falciparum* is attributed to its ability to evade the human immune system by modifying infected erythrocytes to adhere to the vascular endothelium of the host and to undergo antigenic variations of about 60 var genes (including var2CSA) encoding PfEMP1 (Pasternak and Dzikowski, *Int J Biochem Cell Biol*. 2009, 41(7): 1463-6). Therefore, the specific expression of VAR2CSA protein in patients with placental malaria may be the result of the co-evolution of human *Plasmodium falciparum* and humans. Since pl-CSA is mainly expressed on the surface of different types of tumor cells and in their extracellular matrixes (Salanti et al., *Cancer Cell*. 2015, 28(4): 500-14; Ayres Pereira et al., *PLoS Pathog*. 2016, 12(8): e1005831; Seiler et al., *Eur Urol*. 2017, 72(1): 142-150), it is supposed that the targeted binding of VAR2CSA protein to pl-CSA may help to break through the immunosuppression microenvironment of solid tumors. The study by Salanti and his collaborators shows that the drug VDC886 (rVAR2 drug conjugated KT886) obtained by coupling rVAR2 protein to a hemiasterlin toxin analogue KT886 from sponge Hemiasterella minor exhibits anti-tumor activity in a non-pregnant tumor-bearing mouse model for non-Hodgkin's lymphoma, prostate cancer and metastatic breast cancer, and has no adverse reactions (Salanti et al., *Cancer Cell.* 2015, 28(4): 500-14). Another study on VDC886 also shows that in in vitro experiments, VDC886 can effectively eliminate cultured muscle invasive bladder cancer (MIBC) cell lines, and IC50 is at a low nanomolar concentration level; and in in vivo experiments, the intravenous injections of VDC886 twice weekly (four times in total) effectively inhibits the growth of orthotopic bladder cancer xenografts with chemoresistance (resistance to cisplatin-based neoadjuvant chemotherapy) and prolongs the survival cycle of tumor-bearing mice (Seiler et al., *Eur Urol.* 2017, 72(1): 142-150). The above studies show that rVAR2 protein has certain stability in tumor-bearing mice, and its immunogenicity has no adverse effects on mice.

Common CAR-T cells mainly phosphorylate signal transduction through the interaction of the CAR with tumor cell surface antigens, to stimulate the cytokine release and cell proliferation of CAR-T cells and ultimately kill or eliminate tumor cells (Chmielewski et al. al., *Immunol Rev.* 2014, 257(1): 83-90). CN105753991A has disclosed an anti-placental chondroitin sulfate chimeric antigen receptor and a use thereof. It is found that CART-rVAR2 obtained by replacing a single-chain fragment variable (ScFv) antibody fragment in common CAR-T cells with a domain of VAR2CSA protein that specifically interacts with pl-CSA has in vitro killing activity for multiple different types of tumor cells. However, follow-up studies have found that CART-rVAR2 does not secrete cytokines.

An existing CAR-T cell technology has limitations below.

1. In clinical trials, most CAR-T cells only target particular tumor types and/or particular protein targets (clinicaltrials.gov), such as CAR-T for targets CD19 and CD22 of B-cell acute lymphoblastic leukemia and B-cell lymphoma (ClinicalTrials.gov Identifier: NCT00450944); CAR-T for a target GPC3 of liver cancer (ClinicalTrials.gov Identifier: NCT02723942); CAR-T expressing an anti-PD1 antibody for lung cancer, liver cancer and gastric cancer (ClinicalTrials.gov Identifier: NCT02862028); CAR-T for GD2-positive glioma patients (ClinicalTrials.gov Identifier: NCT03252171); CAR-T for EphA2-positive malignant glioma patients (ClinicalTrials.gov Identifier: NCT02575261); therapeutic CAR-T for a target MUC1 of lung cancer (ClinicalTrials.gov Identifier: NCT03198052); therapeutic CAR-T for a target BCMA of multiple myeloma (ClinicalTrials.gov Identifier: NCT03070327); therapeutic CAR-T for a target CD123 of acute myelogenous leukemia (ClinicalTrials.gov Identifier: NCT03190278); therapeutic CAR-T for a target EGFRvIII of glioblastoma (NCT02209376, NCT02664363); and therapeutic CAR-T for targets CD138 and BCMA of multiple myeloma (ClinicalTrials.gov Identifier: NCT03196414).

2. The CAR-T has serious toxic side effects described below. (1) Toxicity to normal tissue cells with low expression of CAR-T cell target protein (tumor-associated antigen), the so-called "on-target, off-tumor toxicities" effect. For example, the treatment of acute B lymphocytic leukemia with CAR-T targeting CD19, whether in mouse models (Davila et al., *PLoS One.* 2013, 8(4): e61338) or in clinical therapy (Brentjens et al., *Blood.* 2011, 118(18): 4817-28), has observed B cell proliferation obstacles. (2) During the construction of CAR-T cells, the use of lentivirus vectors or other retroviral vectors may cause the possibility of cell canceration due to gene insertional mutagenesis. For example, in a clinical trial using a retrovirus for treating a severe combined immunodeficiency disease due to the deletion of a γ chain common to cytokine receptors, it was found that four of nine patients treated with $CD34^+$ bone marrow progenitor cells transduced by the retrovirus developed acute T cell leukemia, and the appearance of this disease was believed to be related to the proliferation in large amounts of the $CD34^+$ bone marrow progenitor cells transduced by the retrovirus due to the insertional mutagenesis of LMO2 proto-oncogenes (Hacein-Bey-Abina et al., *N Engl J Med.* 2003, 348(3): 255-6; Hacein-Bey-Abina et al., *N Engl J Med.* 2010, 363(4): 355-64). (3) A powerful killing effect of CAR-T cells on tumor cells results in serious adverse reactions, called an "on-target, on-tumor toxicities" effect, such as a tumor lysis syndrome (TLS) (Kochenderfer et al., *Blood.* 2013, 122(25): 4129-39), a cytokine release syndrome (CRS) (Maude et al., *N Engl J Med.* 2014, 371(16): 1507-17), and a related macrophage activation syndrome (MAS) (Grupp et al., *ASH Annu Meet Abstr.* 2012, 120(21): 2604). A "suicide gene switch"-type CAR-T cells constructed by a regulatory system based on inducible Caspase 9 (iCasp9) protein is said to be able to effectively inhibit the "on-target, on-tumor toxicities" effect by clearing transduced CAR-T cells (Gargett and Brown, *Front. Pharmacol.* 2014, 5(235): 1-7; Tey, Clin Transl Immunology. 2014, 3(6): e17). However, the effectiveness and necessity of iCasp9 in CAR-T cell therapy need further verification (Ledford, *Nature.* 2016, 538(7624): 150-151; Paszkiewicz et al., *J Clin Invest.* 2016, 126(11): 4262-4272). It is also an effective strategy to co-express another protein molecule on CAR-T cells and then use the protein-specific neutralizing antibody to eliminate CAR-T cells tagged with the protein, for example, an anti-CD20 chimeric antibody rituximab is used for eliminating CD20-expressing T cells (Vogler et al, *Mol Ther.* 2010, 18(7): 1330-1338; Philip et al. *Blood.* 2014, 124(8): 1277-1287), and an anti-Myc-tag antibody is used for eliminating Myc-tag-expressing T cells (Kieback et al., *Proc Natl Acad Sci USA.* 2008, 105(2): 623-628). However, the anti-CD20 chimeric antibody may be difficult to be applied to the CAR-T targeting B lymphocyte tumors, and the Myc-tag strategy lacks clinical antibodies (Paszkiewicz et al., *J Clin Invest.* 2016, 126(11): 4262-4272) A truncated human epidermal growth factor receptor polypeptide (tEGFR) that only retains an intact binding site for cetuximab (Erbitux™) and does not include the extracellular N-terminal ligand binding domain and the intracellular receptor tyrosine kinase domain of the cetuximab (Erbitux™) is linked to a 2A sequence and expressed on CAR-T cells as a cell surface marker for the enrichment and tracking identification of CARtT cells infused in vivo, and the clinical cetuximab may be used for controlling the in vivo activity of the infused CARtT cells through antibody-dependent cytotoxicity (Wang et al., *Blood.* 2011, 118(5): 1255-63). However, in the case of severe toxicity, whether the apoptosis through antibody-dependent cytotoxicity can be started quickly needs to be verified in clinical trials.

3. Application of CAR T cells for the treatment of solid tumors remains a challenge (Newick et al., *Annu Rev Med.* 2017, 68:139-152). Different from the situation in hematologic malignancies, CAR-T cells must reach solid tumor sites through a blood system and infiltrate and penetrate tumor stroma in order to produce tumor-associated antigen-specific cytotoxicity and kill tumor cells. However, though CAR-T cells are successfully transported and infiltrated to the solid tumor sites, the function of CAR-T cells will be quickly lost for the following reasons: (1) the suppression of the tumor microenvironment: the activity of T cells will be suppressed by oxidative stress responses, malnutrition, the acidic pH environment, hypoxia, etc. of the tumor microenvironment; (2) the negative effects of soluble T cell inhibitory factors and cytokines; (3) the inhibitory effect of suppressive immune cells, such as regulatory T cells (Tregs), myeloid-derived suppressor cells (MDSCs), tumor-associated macrophages (TAMs) or tumor-associated neutrophils (TANs); and (4) a T cell's own endogenous negative regulatory mechanism, such as the inhibitory effect generated by up-regulating the expression of intracellular and cell surface inhibitory receptors.

Therefore, common CAR-T technologies are substantially individualized treatment technologies and tend to be accompanied by serious toxic side effects and even threaten the lives of patients in the treatment process. The CAR-T cellular therapy for solid tumors is still a difficulty. How to develop general CAR-T cells with killing activity for many different types of tumors and reduce the toxic side effects of the CAR-T cells is an urgent problem to be solved.

SUMMARY

Facing the possibility that at present, CAR-T technologies are accompanied by serious toxic side effects and even threaten the lives of patients in the treatment of tumors, the present invention provides a chimeric antigen receptor and a use thereof. The chimeric antigen receptor has an ability of targeting multiple different types of tumor cells, has generality that common CAR-T cells do not have, and is switchable.

To achieve the object, the present invention adopts solutions described below.

In a first aspect, the present invention provides a chimeric antigen receptor, where the chimeric antigen receptor contains a domain which identifies any one or a combination of at least two of a malarial protein VAR2CSA (also known as *Plasmodium* protein VAR2CSA), a protein tag on the malarial protein VAR2CSA, or a compound capable of labeling the malarial protein VAR2CSA.

In the present invention, the chimeric antigen receptor includes a binding domain capable of identifying the malarial protein VAR2CSA. It can identify the VAR2CSA protein by identifying a recombinant protein (rVAR2) of any one or at least two domains in the VAR2CSA protein that can bind to the placental-like chondroitin sulfate A (pl-CSA), and can also identify a marker molecule on the malarial protein VAR2CSA, that is, a fusion protein tag that can be recombinant and expressed with the malarial protein VAR2CSA or the compound capable of labeling the malarial protein VAR2CSA. That is to say, chimeric antigen receptors that can identify the VAR2CSA protein in any way are within the scope of the present application, and whether to identify the VAR2CSA protein itself or identify other proteins that can be fused with the VAR2CSA protein or the compound capable of labeling the VAR2CSA protein is within the scope of the present invention.

In the present invention, the VAR2CSA protein has the ability of targeting multiple different types of tumor cells by binding to the placental-like chondroitin sulfate A (pl-CSA) on the surface of tumor cells. Almost 95% (106/111) of human tumor cells which are derived from cancer patients, including those derived from a hematopoietic system, epithelial tissues and mesenchyme can all be targeted.

In the present invention, the inventor has found by specifically binding the chimeric antigen receptor to the VAR2CSA protein that the content of the VAR2CSA protein may be adjusted to further adjust the effect of the chimeric antigen receptor. In the absence of the VAR2CSA protein, the chimeric antigen receptor will not effect and thus has no toxic side effects on human healthy cells.

In the present invention, the protein tag and the VAR2CSA protein are fused and expressed to produce a fusion protein, so that the domain of the chimeric antigen receptor that can identify the protein tag can indirectly identity the VAR2CSA fusion protein containing the protein tag. Similarly, the VAR2CSA protein is labeled with a compound, and then a single chain fragment variable antibody that can specifically identify the compound is used for constructing the chimeric antigen receptor, so that the VAR2CSA protein containing the compound can be indirectly identified.

According to the present invention, the domain which identifies the malarial protein VAR2CSA contains a variable heavy chain ($V_H$) and a variable light chain ($V_L$) of an anti-VAR2CSA antibody.

According to the present invention, an antigen of the anti-VAR2CSA antibody is any one or a combination of at least two of DBL1X, ID1, DBL2X, ID2a, ID2b, DBL3X, ID3, DBL4ε, ID4, DBL5ε, ID5, or DBL6ε, preferably, a combination of ID1, DBL2X and ID2a.

In the present invention, the inventor has found that the VAR2CSA protein may be identified by identifying any one fragment of the VAR2CSA protein, especially the combination of ID1, DBL2X and ID2a, that is, the recombinant protein (rVAR2) of any one or at least two domains in the VAR2CSA protein that can bind to the placental-like chondroitin sulfate A (pl-CSA), so that the VAR2CSA protein can be accurately identified. Moreover, the rVAR2 can bind to the placental-like chondroitin sulfate A (pl-CSA) on the surface of tumor cells, and thus can also be used as an intermediate for the chimeric antigen receptor to target the pl-CSA antigen on the surface of tumor cells.

Preferably, the DBL1X contains an amino acid sequence as shown by SEQ ID NO. 1, where the amino acid sequence as shown by SEQ ID NO. 1 is as follows:

```
DBL1X (SEQ ID NO. 1):
SGTNDPCDRIPPPYGDNDQWKCAIILSKVSEKPENVFVPPRRQRMCINN

LEKLNVDKIRDKHAFLADVLLTARNEGERIVQNHPDTNSSNVCNALERS

FADIADIIRGTDLWKGTNSNLEQNLKQMFAKIRENDKVLQDKYPKDQNY

RKLREDWWNANRQKVWEVITCGARSNDLLIKRGWRTSGKSNGDNKLELC

RKCGHYEEKVPTKLDYVPQFLRWLTEWIEDFYREKQNLIDDMERHREEC

TSEDHKSKEGTSYCSTCKDKCKKYCECVKKWKSEWENQKNKYTELYQQN

KNETSQKNTSRYDDYVKDFFKKLEANYSSLE.
```

Preferably, the ID1 contains an amino acid sequence as shown by SEQ ID NO. 2, where the amino acid sequence as shown by SEQ ID NO. 2 is as follows:

```
ID1 (SEQ ID NO. 2):
NYIKGDPYFAEYATKLSFILNSSDANNPSEKIQKNNDEVCNCNESGIAS

VEQEQISDPSSNKTCITHSSIKANKKKVCKHVKLGVRENDKDLRVCVIE

HTSLSGVENCCCQDFLRILQENCSDNKSGSSSNGSCNNKNQEACEKNLE

KVLAS.
```

Preferably, the DBL2X contains an amino acid sequence as shown by SEQ ID NO. 3, where the amino acid sequence as shown by SEQ ID NO. 3 is as follows:

```
DBL2X (SEQ ID NO. 3):
LTNCYKCDKCKSEQSKKNNKNWIWKKSSGKEGGLQKEYANTIGLPPRTQ

SLCLVVCLDEKGKKTQELKNIRTNSELLKEWIIAAFHEGKNLKPSHEKK

NDDNGKKLCKALEYSFADYGDLIKGTSIWDNEYTKDLELNLQKIFGKLF

RKYIKKNNTAEQDTSYSSLDELRESWWNTNKKYIWLAMKHGAGMNSTTC

CGDGSVTGSGSSCDDIPTIDLIPQYLRFLQEWVEHFCKQRQEKVKPVIE

NCKSCKESGGTCNGECKTECKNKCEVYKKFIEDCKGGDGTAGSSWVKRW

DQIYKRYSKYIEDAKRNRKAGTKNCGPSSTTNAAENKCVQSDIDSFFKH

LIDIG.
```

Preferably, the ID2a contains an amino acid sequence as shown by SEQ ID NO. 4, where the amino acid sequence as shown by SEQ ID NO. 4 is as follows:

```
ID2a (SEQ ID NO. 4):
LTTPSSYLSIVLDDNICGADKAPWTTYTTYTTTEKCNKETDKSKLQQCN

TAVVVNVPSPLGNTPHGYKYACQCKIPTNEETCDDRKEYMNQWSCGSAR

TMKRGYKNDNYELCKYNGVDVKPTTVRSNSSKLD.
```

Preferably, the ID2b contains an amino acid sequence as shown by SEQ ID NO. 5, where the amino acid sequence as shown by SEQ ID NO. 5 is as follows:

```
ID2b (SEQ ID NO. 5):
DKDVTFFNLFEQWNKEIQYQIEQYMTNTKISCNNEKNVLSRVSDEAAQP

KFSDNERDRNSITHEDKNCKEKCKCYSLWIEKINDQWDKQKDNYNKFQR

KQIYDANKGSQNKKVVSLSNFLFFSCWEEYIQKYFNGDWSKIKNIGSDT

FEFLIKKCGNDSGDGETIFSEKLNNAEKKCKENESTNNKMKSSETS.
```

Preferably, the DBL3X contains an amino acid sequence as shown by SEQ ID NO. 6, where the amino acid sequence as shown by SEQ ID NO. 6 is as follows:

```
DBL3X (SEQ ID NO. 6):
CDCSEPIYIRGCQPKIYDGKIFPGKGGEKQWICKDTIIHGDTNGACIPP

RTQNLCVGELWDKRYGGRSNIKNDTKESLKQKIKNAIQKETELLYEYHD

KGTAIISRNPMKGQKEKEEKNNDSNGLPKGFCHAVQRSFIDYKNMILGT

SVNIYEYIGKLQEDIKKIIEKGTTKQNGKTVGSGAENVNAWWKGIEGEM

WDAVRCAITKINKKQKKNGTFSIDECGIFPPTGNDEDQSVSWFKEWSEQ

FCIERLQYEKNIRDACTNNGQGDKIQGDCKRKCEEYKKYISEKKQEWDK

QKTKYENKYVGKSASDLLKENYPECISANFDFIFNDNIEYKTYYPYGDY

SSICSCEQVKYYEYNNAEKKNNKSL.
```

Preferably, the ID3 contains an amino acid sequence as shown by SEQ ID NO. 7, where the amino acid sequence as shown by SEQ ID NO. 7 is as follows:
ID3 (SEQ ID NO. 7):
CHEKGNDRTWSKKYIKKL.

Preferably, the DBL4ε contains an amino acid sequence as shown by SEQ ID NO. 8, where the amino acid sequence as shown by SEQ ID NO. 8 is as follows:

```
DBL4ε (SEQ ID NO. 8):
ENGRTLEGVYVPPRRQQLCLYELFPIIIKNKNDITNAKKELLETLQIVA

EREAYYLWKQYHAHNDTTYLAHKKACCAIRGSFYDLEDIIKGNDLVHDE

YTKYIDSKLNEIFDSSNKNDIETKRARTDWWENEAIAVPNITGANKSDP

KTIRQLVWDAMQSGVRKAIDEEKEKKKPNENFPPCMGVQHIGIAKPQFI

RWLEEWTNEFCEKYTKYFEDMKSNCNLRKGADDCDDNSNIECKKACANY

TNWLNPKRIEWNGMSNYYNKIYRKSNKESEDGKDYSMIMEPTVIDYLNK

RCNGEINGNYICCSCK.
```

Preferably, the ID4 contains an amino acid sequence as shown by SEQ ID NO. 9, where the amino acid sequence as shown by SEQ ID NO. 9 is as follows:

```
ID4 (SEQ ID NO. 9):
NIGENSTSGTVNKKLQKKETQCEDNKGPLDLMNKVLNKMDPKYSEHKMK

CTEVYLEHVEEQLKEIDNAIKDYKLYPLDRCFDDKS.
```

Preferably, the DBL5ε contains an amino acid sequence as shown by SEQ ID NO. 10, where the amino acid sequence as shown by SEQ ID NO. 10 is as follows:

```
DBL5ε (SEQ ID NO. 10):
KMKVCDLIGDAIGCKHKTKLDELDEWNDVDMRDPYNKYKGVLIPPRRRQ

LCFSRIVRGPANLRNLKEFKEEILKGAQSEGKFLGNYYNEDKDKEKALE

AMKNSFYDYEYIIKGSDMLTNIQFKDIKRKLDRLLEKETNNTEKVDDWW

ETNKKSIWNAMLCGYKKSGNKIIDPSWCTIPTTETPPQFLRWIKEWGTN

VCIQKEEHKEYVKSKCSNVTNLGAQESESKNCTSEIKKYQEWSRKRSIQ

WEAISEGYKKYKGMDEFKNTFKNIKEPDANEPNANEYLKKHCSKCPCGF

NDMQ.
```

Preferably, the ID5 contains an amino acid sequence as shown by SEQ ID NO. 11, where the amino acid sequence as shown by SEQ ID NO. 11 is as follows:

```
ID5 (SEQ ID NO. 11):
EITKYTNIGNEAFKQIKEQVDIPAELEDVIYRLKHHEYDKGNDYICNKY

KNINVNMKKNNDDTWTDLV.
```

Preferably, the DBL6ε contains an amino acid sequence as shown by SEQ ID NO. 12, where the amino acid sequence as shown by SEQ ID NO. 12 is as follows:

```
DBL6ε (SEQ ID NO. 12):
KNSSDINKGVLLPPRRKNLFLKIDESDICKYKRDPKLFKDFIYSSAISE

VERLKKVYGEAKTKVVHAMKYSFADIGSIIKGDDMMENNSSDKIGKILG

DGVGQNEKRKKWWDMNKYHIWESMLCGYKHAYGNISENDRKMLDIPNND

DEHQFLRWFQEWTENFCTKRNELYENMVTACNSAKCNTSNGSVDKKECT

EACKNYSNFILIKKKEYQSLNSQYDMNYKETKAEKKESPEYFKDKCNGE

CSCLSEYFKDETRWKNPYETLDDTEVKNN.
```

According to the present invention, the anti-VAR2CSA antibody is a single chain fragment variable antibody linked by short peptides including 15 to 20 amino acids.

According to the present invention, the malarial protein VAR2CSA binding domain contains complementarity determining region (CDR) sequences of a variable heavy chain and a variable light chain of the anti-VAR2CSA antibody.

According to the present invention, the CDR of the variable heavy chain of the single chain fragment variable antibody has the following sequences: an amino acid sequence CDR1 as shown by SEQ ID NO. 13; an amino acid sequence CDR2 as shown by SEQ ID NO. 14; and an amino acid sequence CDR3 as shown by SEQ ID NO. 15:
CDR1 (SEQ ID NO. 13): GFTFSNYA;
CDR2 (SEQ ID NO. 14): ISITGRYT;
CDR3 (SEQ ID NO. 15): TREGYDYAPSWFAY.

According to the present invention, the CDR of the variable light chain of the single chain fragment variable antibody has the following sequences: an amino acid sequence CDR1 as shown by SEQ ID NO. 16: an amino acid sequence CDR2 as shown by SEQ ID NO. 17; and an amino acid sequence CDR3 as shown by SEQ ID NO. 18:
CDR1 (SEQ ID NO. 16): QTLVHRNGITY:
CDR2 (SEQ ID NO. 17): KVS;
CDR3 (SEQ ID NO. 18): FQGSHVPRT.

According to the present invention, the variable heavy chain of the single chain fragment variable antibody of the VAR2CSA binding domain contains an amino acid sequence as shown by SEQ ID NO. 19 or a variant having at least 70% amino acid sequence identity, preferably at least 90% amino acid sequence identity to the amino acid sequence as shown by SEQ ID NO. 19.

In the present invention, the variant still has the activity for binding to the VAR2CSA protein, and the amino acid sequence as shown by SEQ ID NO. 19 is as follows:

EVKLVESGGGLVKPGGSLKLSCAASGFTFSNYAMSWVRQSPERRLEWVA

EISITGRYTYYPDTVTGRFTISRDNAKNTLYLEMSSLRSEDTAMYYCTR

EGYDYAPSWFAYWGQGTLVTVSA.

According to the present invention, the variable light chain of the single chain fragment variable antibody of the VAR2CSA binding domain contains an amino acid sequence as shown by SEQ ID NO. 20 or a variant having at least 70% amino acid sequence identity, preferably at least 90% amino acid sequence identity to the amino acid sequence as shown by SEQ ID NO. 20.

In the present invention, the variant still has the activity for binding to the VAR2CSA protein, and the amino acid sequence as shown by SEQ ID NO. 20 is as follows:

DVVMTQTPLSLPVSLGDQASISCRSGQTLVHRNGITYLEWYLQKPGQSP

KLLIYKVSNRFSGVPDRFSGSGSGTDFTLKISRVEAEDLGIYYCFQGSH

VPRTFGGGTKLEIK.

According to the present invention, the variable heavy chain of the single chain fragment variable antibody of the VAR2CSA binding domain contains a nucleotide sequence as shown by SEQ ID NO. 21 or a variant having at least 60% nucleotide sequence identity, preferably at least 80% nucleotide sequence identity to the nucleotide sequence as shown by SEQ ID NO. 21.

In the present invention, the variant still has amino acids which can be expressed for binding to the VAR2CSA protein, and the nucleotide sequence as shown by SEQ ID NO. 21 is as follows:

GAGGTGAAGCTGGTGGAGTCTGGGGGAGGCTTAGTGAAGCCTGGAGGGTC

CCTAAAACTCTCCTGTGCAGCCTCTGGATTCACTTTCAGTAACTATGCCA

TGTCTTGGGTTCGCCAGTCTCCAGAGAGGAGGCTGGAGTGGGTCGCAGAA

ATTAGTATTACTGGTCGTTACACCTACTATCCAGACACTGTGACGGGCCG

ATTCACCATCTCCAGAGACAATGCCAAGAACACCCTGTACCTGGAAATGA

GCAGTCTGAGGTCTGAGGACACGGCCATGTATTATTGTACAAGGGAGGGA

TATGACTACGCCCCCTCCTGGTTTGCTTACTGGGGCCAAGGGACTCTGGT

CACTGTCTCTGCA.

According to the present invention, the variable light chain of the single chain fragment variable antibody of the VAR2CSA binding domain contains a nucleotide sequence as shown by SEQ ID NO. 22 or a variant having at least 60% nucleotide sequence identity, preferably at least 80% nucleotide sequence identity to the nucleotide sequence as shown by SEQ ID NO. 22.

In the present invention, the variant still has amino acids which can be expressed for binding to the VAR2CSA protein, and the nucleotide sequence as shown by SEQ ID NO. 22 is as follows:

GATGTTGTGATGACCCAAACTCCACTCTCCCTGCCTGTCAGTCTTGGAGA

TCAAGCCTCCATCTCTTGCAGATCTGGTCAGACCCTTGTACATCGTAATG

GAATCACCTATTTAGAATGGTACCTGCAGAAACCAGGCCAGTCTCCAAAG

CTCCTGATCTACAAAGTTTCCAACCGATTTTCTGGAGTCCCAGACAGGTT

CAGTGGCAGTGGATCAGGGACAGATTTCACACTCAAGATCAGCAGAGTGG

AGGCTGAGGATCTGGGAATTTATTACTGCTTTCAAGGTTCACATGTTCCT

CGGACGTTCGGTGGAGGCACCAAGCTGGAAATCAAA.

Preferably, the protein tag on the malarial protein VAR2CSA is selected from, but not limited to, any one or a combination of at least two of PNE-tag, human myc-tag CaptureSelect C-tag, FLAG-tag, 3×FLAG-tag, Strep-tag, 6×His-tag, V5 tag, S-tag, HA-tag, VSV-G-tag, GST-tag, Halo Tag, XTEN-tag, or huEGFRt-tag.

The PNE-tag (peptide neo-epitopes) includes 14 amino acids on a transcription factor GCN4 from yeast, and has an amino acid sequence as shown by SEQ ID NO. 23, where the amino acid sequence as shown by SEQ ID NO. 23 is as follows:
PNE-tag (SEQ ID NO. 23): NYHLENEVARLKKL.

The human myc-tag includes 10 amino acids from human c-myc protein, and has an amino acid sequence as shown by SEQ ID NO. 24, where the amino acid sequence as shown by SEQ ID NO. 24 is as follows:
Myc-tag (SEQ ID NO. 24): EQKLISEEDL.

The CaptureSelect C-tag includes an amino acid sequence as shown by SEQ ID NO. 25, where the amino acid sequence as shown by SEQ ID NO. 25 is as follows:
CaptureSelect C-tag (SEQ ID NO. 25): EPEA.

The FLAG-tag includes an amino acid sequence as shown by SEQ ID NO. 26, where the amino acid sequence as shown by SEQ ID NO. 26 is as follows:
FLAG-tag (SEQ ID NO. 26): DYKDDDDK.

The 3×FLAG-tag includes an amino acid sequence as shown by SEQ ID NO. 27, where the amino acid sequence as shown by SEQ ID NO. 27 is as follows:

3×FLAG-tag (SEQ ID NO. 27): DYKDHDGDYKDHDI-DYKDDDDK.

The Strep-tag includes an amino acid sequence as shown by SEQ ID NO. 28, where the amino acid sequence as shown by SEQ ID NO. 28 is as follows:

Strep-tag (SEQ ID NO. 28): WSHPQFEK.

The 6×His-tag includes an amino acid sequence as shown by SEQ ID NO. 29, where the amino acid sequence as shown by SEQ ID NO. 29 is as follows:

6×His-tag (SEQ ID NO. 29): HHHHHH.

The V5-tag includes an amino acid sequence as shown by SEQ ID NO. 30, where the amino acid sequence as shown by SEQ ID NO. 30 is as follows:

V5-tag (SEQ ID NO. 30): GKPIPNPLLGLDST.

The S-tag includes an amino acid sequence as shown by SEQ ID NO. 31, where the amino acid sequence as shown by SEQ ID NO. 31 is as follows:

S-tag (SEQ ID NO. 31): KETAAAKFERQHMDS.

The HA-tag includes an amino acid sequence as shown by SEQ ID NO. 32, where the amino acid sequence as shown by SEQ ID NO. 32 is as follows:

HA-tag (SEQ ID NO. 32): YPYDVPDYA.

The VSV-G-tag includes an amino acid sequence as shown by SEQ ID NO. 33, where the amino acid sequence as shown by SEQ ID NO. 33 is as follows:

VSV-G-tag (SEQ ID NO. 33): YTDIEMNRLGK.

The GST-tag includes an amino acid sequence as shown by SEQ ID NO. 34, where the amino acid sequence as shown by SEQ ID NO. 34 is as follows:

GST-tag (SEQ ID NO. 34):

```
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPK.
```

The HaloTag includes an amino acid sequence as shown by SEQ ID NO. 35, where the amino acid sequence as shown by SEQ ID NO. 35 is as follows:

```
HaloTag (SEQ ID NO. 35):
MAEIGTGFPFDPHYVEVLGERMHYVDVGPRDGTPVLFLHGNPTSSYVWRN

IIPHVAPTHRCIAPDLIGMGKSDKPDLGYFFDDHVRFMDAFIEALGLEEV

VLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDRE

PLWRFPNELPIAGEPANIVALVEEYMDWLHQSPVPKLLFWGTPGVLIPPA

EAARLAKSLPNCKAVDIGPGLNLLQEDNPDLIGSEIARWLSTLEISG.
```

The XTEN-tag includes an amino acid sequence as shown by SEQ ID NO. 36, where the amino acid sequence as shown by SEQ ID NO. 36 is as follows:

```
XTEN-tag (SEQ ID NO. 36):
SPAGSPTSTEEGTSESATPESGPGTSTEPSEGSAPGSPAGSPTSTEEGTS

TEPSEGSAPGTSTEPSEGSAPGTSESATPESGPGSEPATSGSETPGSEPA

TSGSETPGSPAGSPTSTEEGTSESATPESGPGTSTEPSEGSAPGTSTEPS

EGSAPGSPAGSPTSTEEGTSTEPSEGSAPGTSTEPSEGSAPGTSESATPE

SGPGTSTEPSEGSAPGTSESATPESGPGSEPATSGSETPGTSTEPSEGSA

PGTSTEPSEGSAPGTSESATPESGPGTSESATPESGPGSPAGSPTSTEEG

TSESATPESGPGSEPATSGSETPGTSESATPESGPGTSTEPSEGSAPGTS

TEPSEGSAPGTSTEPSEGSAPGTSTEPSEGSAPGTSTEPSEGSAPGTSTE

PSEGSAPGSPAGSPTSTEEGTSTEPSEGSAPGTSESATPESGPGSEPATS

GSETPGTSESATPESGPGSEPATSGSETPGTSESATPESGPGTSTEPSEG

SAPGTSESATPESGPGSPAGSPTSTEEGSPAGSPTSTEEGSPAGSPTSTE

EGTSESATPESGPGTSTEPSEGSAPGTSESATPESGPGSEPATSGSETPG

TSESATPESGPGSEPATSGSETPGTSESATPESGPGTSTEPSEGSAPGSP

AGSPTSTEEGTSESATPESGPGSEPATSGSETPGTSESATPESGPGSPAG

SPTSTEEGSPAGSPTSTEEGTSTEPSEGSAPGTSESATPESGPGTSESAT

PESGPGTSESATPESGPGSEPATSGSETPGSEPATSGSETPGSPAGSPTS

TEEGTSTEPSEGSAPGTSTEPSEGSAPGSEPATSGSETPGTSESATPESG

PGTSTEPSEGSAPG.
```

The huEGFRt-tag includes a truncated human epidermal growth factor receptor polypeptide (tEGFR) that only retains an intact binding site for cetuximab (Erbitux™) and does not include the extracellular N-terminal ligand binding domain and the intracellular receptor tyrosine kinase domain of the cetuximab (Erbitux™), and has an amino acid sequence as shown by SEQ ID NO. 37, where the amino acid sequence as shown by SEQ ID NO. 37 is as follows:

```
huEGFRt-tag (SEQ ID NO. 37):
NIKHFKNCTSISGDLHILPVAFRGDSFTHTPPLDPQELDILKTVKEITGF

LLIQAWPENRTDLHAFENLEIIRGRTKQHGQFSLAVVSLNITSLGLRSLK

EISDGDVIISGNKNLCYANTINWKKLFGTSGQKTKIISNRGENSCKATGQ

VCHALCSPEGCWGPEPRDCVSCRNVSRGRECVDKCNLLEGEPREFVENSE

CIQCHPECLPQAMNITCTGRGPDNCIQCAHYIDGPHCVKTCPAGVMGENN

TLVWKYADAGHVCHLCHPNCTYGCTGPGLEGCPTNGPKIPSIATGMVGAL

LLLLVVALGIGLFM.
```

The compound capable of labeling the malarial protein VAR2CSA refers to that the malarial protein VAR2CSA can be identified through the compound. Those skilled in the art may select the compound according to the malarial protein VAR2CSA. The compound of the present invention may be fluorescein isothiocyanate containing a cyclooctynyl group (BCN-PEG4-FITC) and/or fluorescein isothiocyanate containing N-hydroxyl succinimide (FITC-PEG4-NHS).

The BCN-PEG4-FITC has a molecular formula represented by Formula I:

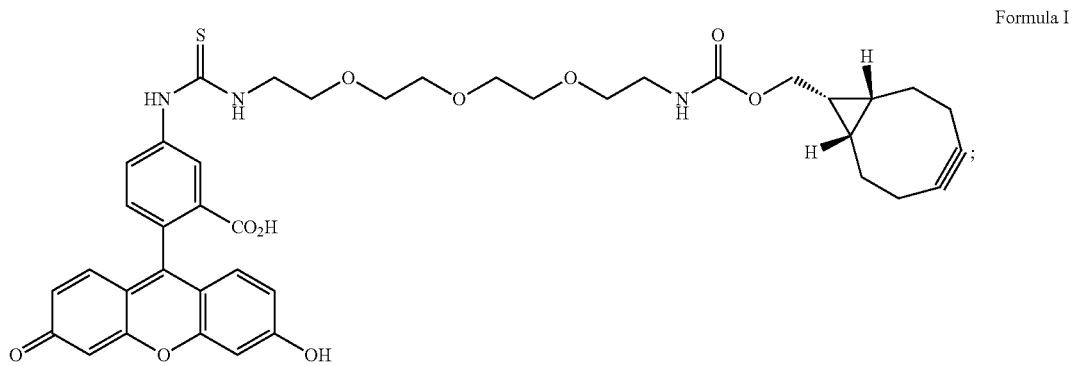 [SMILES: O=C(NCCOCCOCCOCCNC(=S)Nc1ccc(-c2c3ccc(=O)cc-3oc3cc(O)ccc23)c(C(=O)O)c1)OC[C@@H]1[C@@H]2CCC#CCC[C@@H]21]

The FITC-PEG4-NHS has a molecular formula represented by Formula II:

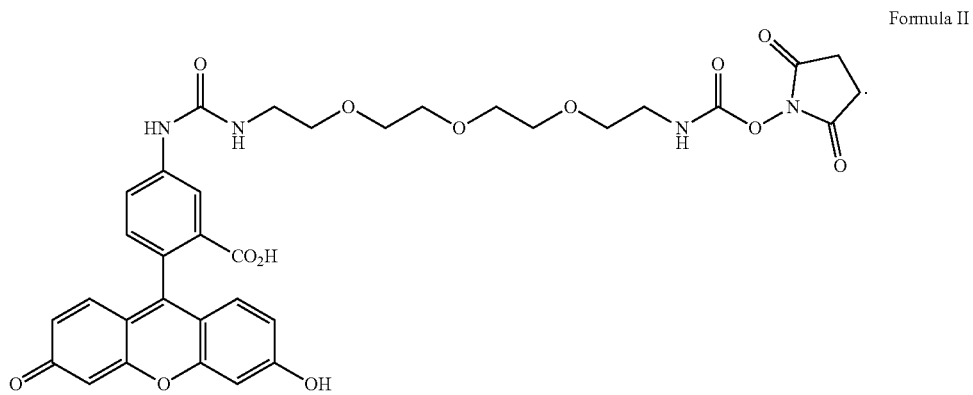 [SMILES: O=C(NCCOCCOCCOCCNC(=O)ON1C(=O)CCC1=O)Nc1ccc(-c2c3ccc(=O)cc-3oc3cc(O)ccc23)c(C(=O)O)c1]

According to the present invention, the chimeric antigen receptor further includes any one or a combination of at least two of a hinge region, a transmembrane domain and an intracellular signaling domain.

According to the present invention, the hinge region is a conventional hinge region, may be selected by those skilled in the art as needed, and is not particularly limited here. The present invention adopts a hinge region of human CD8α.

According to the present invention, the transmembrane domain is a conventional transmembrane domain, may be selected by those skilled in the art as needed, and is not particularly limited here. The present invention adopts a transmembrane domain of human CD28.

According to the present invention, the intracellular signaling domain is a conventional intracellular signaling domain, may be selected by those skilled in the art as needed, and is not particularly limited here. The present invention adopts any one or a combination of at least two of an intracellular signaling domain of human CD27, an intracellular signaling domain of human CD134, an intracellular signaling domain of human CD28, or an intracellular signaling domain of human 4-1BB (CD137).

According to the present invention, the chimeric antigen receptor contains a signaling peptide CD8α at the amino terminus; and the chimeric antigen receptor contains an intracellular signaling domain of human CD3ζ at the carboxyl terminus.

In a second aspect, the present invention provides a nucleic acid encoding the chimeric antigen receptor as described in the first aspect or a nucleic acid having at least 60% identity, preferably at least 80% identity to the nucleic acid.

In the present invention, the nucleic acid can express amino acids which bind to the VAR2CSA protein.

In a third aspect, the present invention provides a chimeric antigen receptor expression cell, where the expression cell contains the nucleic acid as described in the second aspect.

Preferably, the cell is an immune effector cell, more preferably any one or a combination of at least two of a T cell, a B cell, an NK cell, an NKT cell, a dendritic cell or a macrophage.

In a fourth aspect, the present invention provides a recombinant vector, where the recombinant vector contains the nucleic acid as described in the second aspect.

Preferably, the vector is any one or a combination of at least two of a recombinant cloning vector, a recombinant eukaryotic expression plasmid or a recombinant lentiviral vector, preferably the recombinant lentiviral vector. Preferably, the recombinant cloning vector is selected from, but not limited to, any one or a combination of at least two of pUC18, pUC19, pMD19-T, pGM-T, pUC57, pMAX or pDC315.

Preferably, the eukaryotic expression plasmid is selected from, but not limited to, any one or a combination of at least two of a pCDNA3 series vector, a pCDNA4 series vector, a pCDNA5 series vector, a pCDNA6 series vector, a pCI-neo series vector, a pEGFP series vector, a pSPT series vector, a pFLAG-CMV series vector, a pRL series vector, a pUC57 vector, pMAX or pDC315.

Preferably, the recombinant lentiviral vector is selected from, but not limited to, any one or a combination of at least two of a recombinant adenovirus vector, a recombinant adeno-associated virus vector, a recombinant retroviral vector, a recombinant herpes simplex virus vector or a recombinant vaccinia virus vector.

In the present invention, the nucleic acid construct of the chimeric antigen receptor is recombined with the vector, so that the recombinant vector can be transfected into an immune cell to obtain the immune cell expressing the chimeric antigen receptor, so as to achieve the function of the chimeric antigen receptor.

In a fifth aspect, the present invention provides a recombinant virus, containing a recombinant virus obtained by co-transfecting mammalian cells with the recombinant vector as described in the fourth aspect and a packaging helper plasmid.

In a sixth aspect, the present invention provides a chimeric antigen receptor T cell (CAR-T), which is obtained by transfecting the recombinant virus as described in the fifth aspect into T cells to express.

In a seventh aspect, the present invention provides a use of the chimeric antigen receptor as described in the first aspect, the nucleic acid as described in the second aspect, the recombinant vector as described in the fourth aspect or the recombinant virus as described in the fifth aspect for transfecting and amplifying CAR-T cells.

In an eighth aspect, the present invention provides a pharmaceutical composition, including the chimeric antigen receptor as described in the first aspect, the nucleic acid as described in the second aspect, the chimeric antigen receptor expression cell as described in the third aspect or the recombinant vector as described in the fourth aspect, and an optional pharmaceutically acceptable excipient.

In a ninth aspect, the present invention provides a use of the chimeric antigen receptor as described in the first aspect, the nucleic acid as described in the second aspect, the chimeric antigen receptor expression cell as described in the third aspect or the recombinant vector as described in the fourth aspect for preparing a medicament for preventing and/or treating an autoimmune disease or a tumor.

Preferably, the tumor is a solid tumor and/or a hematologic malignancy, and the tumor may be any tumor issue and cell that can be specifically identified and bind to a VAR2CSA protein or a recombinant protein (rVAR2) of any one or at least two domains in the VAR2CSA protein that can bind to a placental-like chondroitin sulfate (CS) glycosaminoglycan (GAG) chain (also known as placenta-like chondroitin sulfate A, abbreviated as pl-CSA). For example, a human lung cancer cell line including NCI-H460 (a large cell lung cancer cell line, ATCC #HTB177), NCI-H520 (a squamous cell lung cancer cell line, ATCC #HTB182) and A549 (a lung adenocarcinoma cell line, ATCC #CCL185) can specifically bind to the rVAR2 protein to different degrees; the rVAR2 protein can also targeted and bind to a human placental choriocarcinoma cell line BeWo (ATCC #CCL98); in addition, a B-cell lymphoma cell line Raji (ATCC #CCL86) and an acute myeloid leukemia cell line KG-1a (ATCC #CCL246.1) can also specifically bind to the rVAR2 protein. However, the rVAR2 protein binds to PBMCs of healthy people and normal human umbilical vein endothelial cells (HUVECs) (ATCC #PCS-100-010) to be negative.

In a tenth aspect, the present invention provides a method for treating a subject suffering from an autoimmune disease and/or a disease related to the expression of a tumor antigen, including administering to the subject an effective amount of a medicament containing the pharmaceutical composition as described in the eighth aspect.

Preferably, the tumor is a solid tumor and/or a hematologic malignancy, and the tumor may be any tumor issue and cell that can be specifically targeted by a VAR2CSA protein or a recombinant protein (rVAR2) of any one or at least two domains in the VAR2CSA protein that can bind to a placental-like chondroitin sulfate A (pl-CSA). For example, the human lung cancer cell lines including NCI-H460 (a large cell lung cancer cell line, ATCC #HTB177), NCI-H520 (a squamous cell lung cancer cell line, ATCC #HTB182) and A549 (a lung adenocarcinoma cell line, ATCC #CCL185) can be specifically bound by the rVAR2 protein to varying degrees; the rVAR2 protein can also target and bind to a human placental choriocarcinoma cell line BeWo (ATCC #CCL98); in addition, a B-cell lymphoma cell line Raji (ATCC #CCL86) and an acute myeloid leukemia cell line KG-1a (ATCC #CCL246.1) can also be specifically targeted by the rVAR2 protein. However, the rVAR2 protein does not bind to peripheral blood mononuclear cells (PBMCs) of healthy people and normal human umbilical vein endothelial cells (HUVECs, ATCC #PCS-100-010).

The term "variant" refers to any variant containing one or more amino acid substitutions, deletions or additions on the premise that the variant essentially retains the same function as an original sequence.

Compared with the existing art, the present invention has beneficial effects described below.

(1) The chimeric antigen receptor of the present invention can identify the VAR2CSA protein or the recombinant protein (rVAR2) of any one or at least two domains in the VAR2CSA protein that can bind to the placental-like chondroitin sulfate A (pl-CSA). The VAR2CSA protein or the rVAR2 protein is capable of targeting several different types of tumor cells by binding to the pl-CSA on the surface of the tumor cells, so as to target almost 95% of human cancer cell lines of cancer patients.

(2) In the present invention, the chimeric antigen receptor specifically binds to the VAR2CSA protein or the recombinant protein (rVAR2) of any one or at least two domains in the VAR2CSA protein that can bind to the placental-like chondroitin sulfate A (pl-CSA) to indirectly identify and kill tumor cells expressing surface antigens containing the pl-CSA. The content of the VAR2CSA protein can be adjusted to further adjust the effect of the chimeric antigen receptor. In the absence of the VAR2CSA protein, the chimeric antigen receptor will not effect and thus has no toxic side effects on human healthy cells.

(3) The extracellular recognition domain of the chimeric antigen receptor of the present invention, that is, the single chain fragment variable antibody (ScFv) can compete with a homologous monoclonal antibody to bind to the binding domain on the VAR2CSA protein or the rVAR2 protein that is targeted by the ScFv, so that the function of chimeric antigen receptor cells can be indirectly limited and adjusted by adjusting the content of the monoclonal antibody of the VAR2CSA protein, which is beneficial to reduce toxic side effects of immune cells such as T cells expressing the chimeric antigen receptor.

(4) In the present invention, the chimeric antigen receptor specifically binds to the VAR2CSA protein or the recombinant protein (rVAR2) of any one or at least two domains in the VAR2CSA protein that can bind to the placental-like chondroitin sulfate A (pl-CSA) to indirectly identify and kill tumor cells expressing surface antigens containing the pl-CSA. The VAR2CSA protein or the recombinant protein (rVAR2) of VAR2CSA-associated domains can be coupled to cytotoxins to clear cells expressing the chimeric antigen receptor redundantly in the body of a cured patient after immunotherapy and reduce the off-target risk.

(5) The chimeric antigen receptor of the present invention can identify the VAR2CSA protein or the recombinant protein (rVAR2) of any one or at least two domains in the VAR2CSA protein that can bind to the placental-like chondroitin sulfate A (pl-CSA). The VAR2CSA or rVAR2 protein specifically targets and binds to the pl-CSA that widely exists in large amounts on the cell surface and extracellular matrix of tumor tissues, so that the chimeric antigen receptor has the potential to target the tumor microenvironment under the synergistic effect of the VAR2CSA protein and immune cells expressing the chimeric antigen receptor, and may help the immune cells expressing the chimeric antigen receptor to break through the immunosuppressive microenvironment of solid tumors, thereby targeting and killing solid tumor cells.

(6) The chimeric antigen receptor of the present invention can be used as a medicament for treating cancer, and has adjustable effects, thereby providing a new idea for cancer treatment.

BRIEF DESCRIPTION OF DRAWINGS

FIG. 1 (A) shows the 10% SDS-PAGE protein gel electrophoresis analysis result of the prokaryotically expressed and purified rVAR2 recombinant protein with a Strep-tag protein tag, and FIG. 1 (B) shows the 10% SDS-PAGE protein gel electrophoresis analysis result of the eukaryotically expressed and purified rVAR2 recombinant protein with a 3×FLAG-tag protein tag, FIG. 2 shows detection of the function of murine anti-rVAR2 protein antibody using enzyme-linked immunosorbent assay (ELISA), wherein NC is the negative control for the ELISA detection obtained by diluting the serum of un-immunized mice at a ratio of 1:500, and the remaining groups are different dilution ratios of the antibody in the experimental group, and wherein the coating concentration of antigen (rVAR2 recombinant protein) in all control and experimental groups is 1 μg/ml;

FIG. 7 (B) is a schematic diagram showing several different types of T cells constructed using the chimeric antigen receptor of the present invention and the binding mode among them and VAR2CSA full-length protein (or its pl-CSA binding domain recombinant protein rVAR2) and tumor cells expressing pl-CSA epitope;

FIG. 9 (B) is Western blot detection of the stability of rVAR2 recombinant protein in human serum;

FIG. 11 (B) shows the detection of secretion levels of IFN-γ in the process of incubation of sCART-anti-rVAR2 (5H4 ScFv) system with Raji cells;

DETAILED DESCRIPTION

Figure 3:
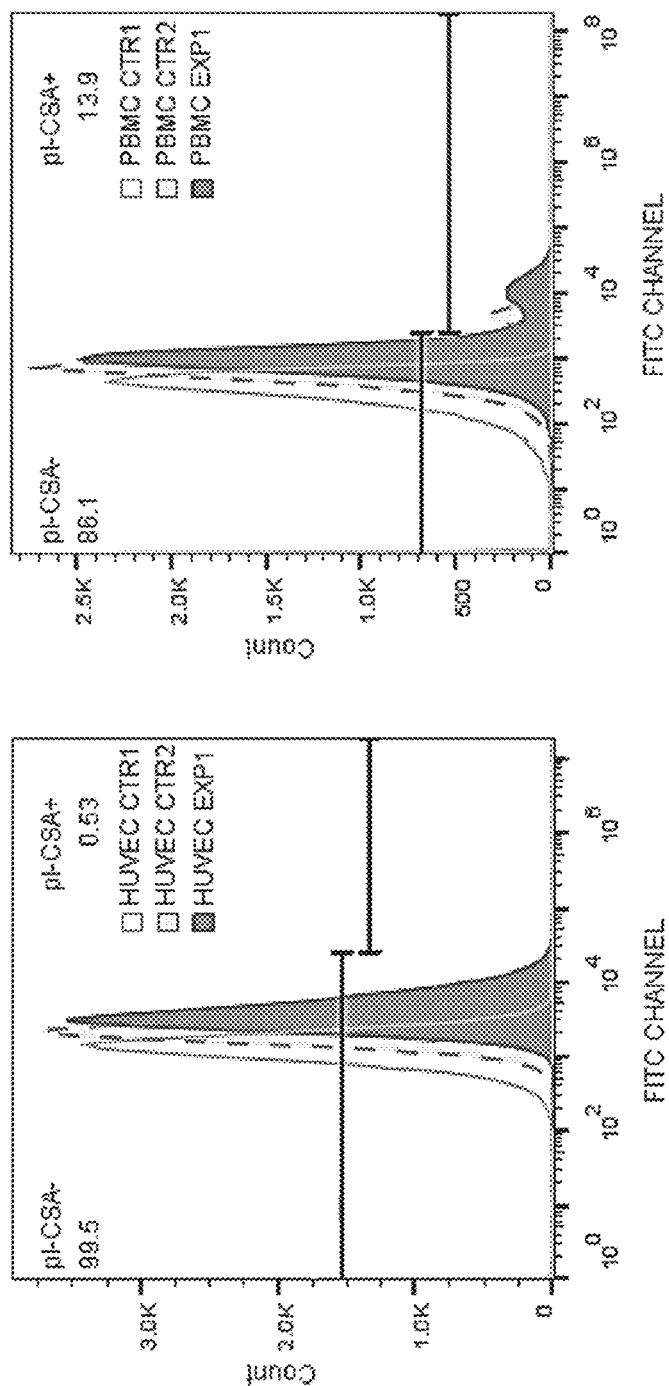
FIG. 3 shows detection of the targeting specificity of rVAR2 protein to tumor cells using flow cytometry.
Figure 3:
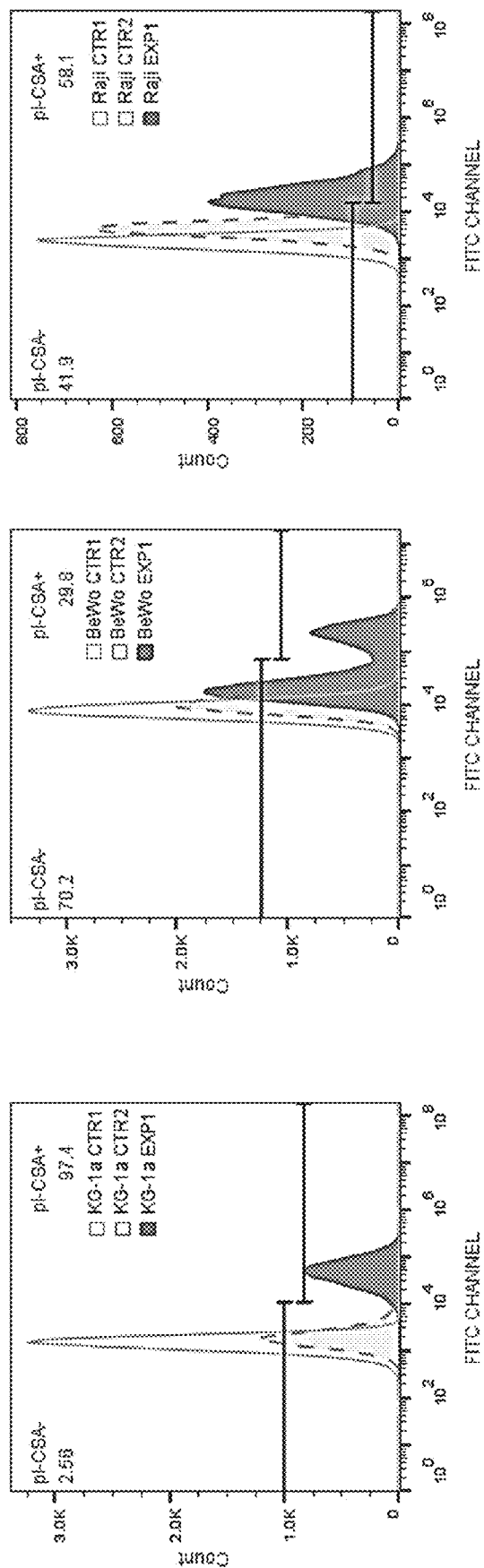
Figure 3:
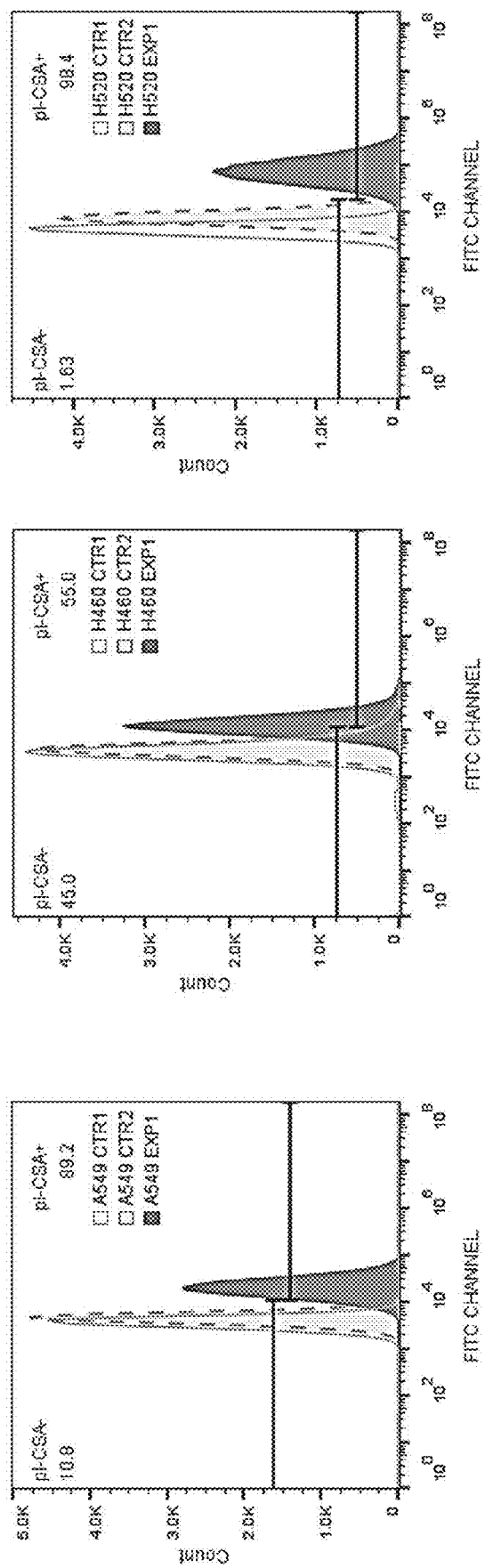

To further elaborate on the technical means adopted and the effects achieved in the present invention, the technical solutions of the present invention are further described below with reference to the drawings and specific embodiments, but the present invention is not limited to the scope of the embodiments.

Example 1: Expression and Purification of Recombinant Proteins Related to the pl-CSA Binding Domain of VAR2CSA Protein First, the DNA molecule encoding the amino acid sequence of the relevant recombinant protein (rVAR2) of the pl-CSA binding domain of the VAR2CSA protein was cloned into a prokaryotic or eukaryotic expression vector. Then the constructed prokaryotic expression vector was transduced into *E. coli* (such as BL21(DE3)), and the constructed eukaryotic expression vector was transduced into eukaryotic cells (such as human embryonic kidney cell line HEK293T containing large T antigen) respectively for protein expression. The protein expressing cells or medium supernatant was collected. Then corresponding protein tag affinity media was used for protein purification with steps as follows:

Strep-Tag Affinity Purification System:

First, *E. coli* expressing rVAR2 recombinant protein with Strep-tag was collected by centrifugation. Pre-cooled Buffer W (100 mM Tris/HCl, pH 8.0, 150 mM NaCl, 1 mM EDTA) was added at 10 ml per gram of cells to re-suspend *E. coli* cells. The suspension was crushed 2-3 times with AH-1500 ultra-high pressure homogenizer (ATS Engineering Inc.) under a pressure of 100 Mpa at a low temperature to obtain cell lysate. The cell lysate supernatant was collected by centrifugation for 10 min at 14,000 rpm, 4° C. Strep-Tactin resin was washed with 2 resin volumes of Buffer W (100 mM Tris/HCl, pH 8.0, 150 mM NaCl, 1 mM EDTA) and equilibrated. The collected cell lysate supernatant was incubated with the equilibrated Strep-Tactin resin for 30 min-1 h, and then allowed to pass through the column. After the penetrating solution was all flowed out, at least 5 Strep-Tactin resin volumes of pre-cooled Buffer W (100 mM Tris/HCl, pH 8.0, 150 mM NaCl, 1 mM EDTA) was added portion-wise to wash the resin. 3 Strep-Tactin resin volume of pre-cooled Buffer E (100 mM Tris/HCl, pH 8.0, 150 mM NaCl, 1 mM EDTA, 2.5 mM desthiobiotin) was added to elute and collect the rVAR2 recombinant protein with Strep-tag from the Strep-Tactin resin in 3 times. Then a certain amount of the purified sample of strep-tagged rVAR2 recombinant protein—was analyzed by SDS-PAGE protein gel electrophoresis. The results were shown in FIG. 1(A). The predicted average molecular weight of the strep-tagged rVAR2 recombinant protein is about 74 kDa.

The amino acid sequence of the rVAR2 recombinant protein with a Strep-tag is as follows (SEQ ID NO.38):

MVHSNYIKGDPYFAEYATKLSFILNSSDANNPSEKIQKNNDEVCNCNESG

IASVEQEQISDPSSNKTCITHSSIKANKKKVCKHVKLGVRENDKDLRVCV

IEHTSLSGVENCCCQDFLRILQENCSDNKSGSSSNGSCNNKNQEACEKNL

EKVLASLTNCYKCDKCKSEQSKKNNKNWIWKKSSGKEGGLQKEYANTIGL

PPRTQSLCLVVCLDEKGKKTQELKNIRTNSELLKEWIIAAFHEGKNLKPS

HEKKNDDNGKKLCKALEYSFADYGDLIKGTSIWDNEYTKDLELNLQKIFG

KLFRKYIKKNNTAEQDTSYSSLDELRESWWNTNKKYIWLAMKHGAGMNST

TCCGDGSVTGSGSSCDDIPTIDLIPQYLRFLQEWVEHFCKQRQEKVKPVI

ENCKSCKESGGTCNGECKTECKNKCEVYKKFIEDCKGGDGTAGSSWVKRW

DQIYKRYSKYIEDAKRNRKAGTKNCGPSSTTNAAENKCVQSDIDSFFKHL

IDIGLTTPSSYLSIVLDDNICGADKAPWTTYTTYTTTEKCNKETDKSKLQ

QCNTAVVVNVPSPLGNTPHGYKYACQCKIPTNEETCDDRKEYMNQWSCGS

ARTMKRGYKNDNYELCKYNGVDVKPTTVRSNSSKLD<u>LEVDLQGDHGLSAW</u>

<u>SHPQFEK</u>.

The black and bold amino acid sequences are the amino acid sequences expressed by the vector backbone DNA introduced during the gene cloning process, and the underlined amino acid sequence is the Strep-tag sequence (SEQ ID NO.28). The rVAR2 recombinant protein with a Strep-tag was purified via the affinity of the Strep-tag II peptide and Strep-Tactin resin.

3×FLAG-Tag Affinity Purification System:

A eukaryotic (mammalian cell) protein expression vector with secreted signal peptide or non-secreted signal peptide was used to construct an expression vector of rVAR2 recombinant protein with 3×FLAG-tag. The expression vector was transfected into HEK293 cells or HEK293T cells by means of electroporation or PEI transfection to express rVAR2 recombinant protein with 3×FLAG-tag. Then the cell culture supernatant (for secreted expression vectors) or cells (for non-secretory vectors) were collected, respectively. 5% of pH-adjusted buffer (1 M Tris-HCl, 3 M NaCl, pH 7.4) was added to the cell culture supernatant for later use. A cell lysis buffer—Buffer L (50 mM Tris HCl, pH 7.4, with 150 mM NaCl, 1 mM EDTA, 1% TRITON X-100, and 1% protease Inhibitor (Sigma, Cat. #P8340)) was added to the collected cells at a ratio of $10^6$-$10^7$ cells/ml, followed by incubation at room temperature for 30 min. Centrifuged at 12,000×g, 4° C. for 10 min to collect the supernatant from cell lysate for later use.

The prepared expression supernatant or cell lysate supernatant containing rVAR2 recombinant protein with a 3×FLAG-tag was incubated with equilibrated affinity resin coupled to ANTI-FLAG M2 antibody or magnetic beads (Sigma) coupled to ANTI-FLAG M2 antibody on ice for 2 hours, and then allowed to pass through a column, or resin or magnetic beads binding to rVAR2 recombinant protein with a 3×FLAG-tag were collected with a magnetic stand. The collected resin or magnetic beads were washed with 20 volumes of TBS buffer (50 mM Tris HCl, 150 mM NaCl, pH 7.4) in three times, and eluted with 5 volumes of 3×FLAG peptide eluent (prepared with TBS buffer, the 3×FLAG peptide concentration was 150 ng/µl), and rVAR2 recombinant protein with 3×FLAG-tag was collected. Then a certain amount of the purified sample of rVAR2 recombinant protein with a 3×FLAG-tag was analyzed by SDS-PAGE protein gel electrophoresis. The results were shown in FIG. 1(B). The predicted average molecular weight of the rVAR2 recombinant protein with a 3×FLAG-tag is about 76 kDa, while 10% of the molecular weight detected by SDS-PAGE gel electrophoresis was about 115 kDa, indicating that there may be post-translational modification for the protein.

The amino acid sequence of the rVAR2 recombinant protein with the 3×FLAG-tag is as follows (SEQ ID NO.39):

MVHSNYIKGDPYFAEYATKLSFILNSSDANNPSEKIQKNNDEVCNCNESG

IASVEQEQISDPSSNKTCITHSSIKANKKKVCKHVKLGVRENDKDLRVCV

IEHTSLSGVENCCCQDFLRILQENCSDNKSGSSSNGSCNNKNQEACEKNL

EKVLASLTNCYKCDKCKSEQSKKNNKNWIWKKSSGKEGGLQKEYANTIGL

PPRTQSLCLVVCLDEKGKKTQELKNIRTNSELLKEWIIAAFHEGKNLKPS

HEKKNDDNGKKLCKALEYSFADYGDLIKGTSIWDNEYTKDLELNLQKIFG

KLFRKYIKKNNTAEQDTSYSSLDELRESWWNTNKKYIWLAMKHGAGMNST

TCCGDGSVTGSGSSCDDIPTIDLIPQYLRFLQEWVEHFCKQRQEKVKPVI

ENCKSCKESGGTCNGECKTECKNKCEVYKKFIEDCKGGDGTAGSSWVKRW

-continued

DQIYKRYSKYIEDAKRNRKAGTKNCGPSSTTNAAENKCVQSDIDSFFKHL

IDIGLTTPSSYLSIVLDDNICGADKAPWTTYTTYTTTEKCNKETDKSKLQ

QCNTAVVVNVPSPLGNTPHGYKYACQCKIPTNEETCDDRKEYMNQWSCGS

ARTMKRGYKNDNYELCKYNGVDVKPTTVRSNSSKLDLEGGGGSGGGGSGG

GGSADYKDHDGDYKDHDIDYKDDDDK.

The black and bold amino acid sequences are the amino acid sequences expressed by the vector backbone DNA introduced during the gene cloning process, and the underlined amino acid sequence is the 3×FLAG-tag sequence (SEQ ID NO.27). The rVAR2 recombinant protein with a 3×FLAG-tag was purified via the affinity of the 3×FLAG-tag and the resins or magnetic beads bound with the ANTI-FLAG M2 antibody.

Example 2: Obtaining Murine-Derived Polyclonal Antibodies and Monoclonal Antibodies Against rVAR2 Protein Three BALB/c mice aged 4-6 weeks were immunized with the prokaryotically expressed and purified rVAR2 recombinant protein. The specific steps are as follows: First, the purified rVAR2 recombinant protein was dialyzed 3 times against phosphate buffered saline (PBS, pH7.4) and the protein was concentrated to 1 μg/μl through ultrafiltration. 100 μl of a solution of the rVAR2 recombinant protein (100 μg) and 100 μl of Freund's complete adjuvant were emulsified, and then mice were injected with the resultant at multiple points on the back for primary immunization. Then 100 μl of a solution of the rVAR2 recombinant protein (100 μg) and 100 μl of Freund's complete adjuvant were emulsified, and then the mice were injected with the resultant at multiple points on the back for 2-3 booster immunization. Then enzyme-linked immunosorbent assay (ELISA) was used to detect the function and titer of the polyclonal antibody in the serum of immunized mice. The results are shown in FIG. 2. With an OD450 value of about 1.0 as the standard, the detected mouse antiserum (polyclonal) titer is about 1:25000.

Appropriate amounts of feeder cells from mouse abdominal cavity and mouse myeloma cells SP2/0 were prepared for later use. Immunized BALB/c mice were anesthetized with isoflurane. Eyeballs were removed to collect blood. Serum was separated for use as a positive control serum during antibody detection. The immunized BALB/c mice were killed by breaking their necks. The spleen was surgically removed and placed in a petri dish containing 10 ml of incomplete culture medium. The spleen was washed gently and surrounding connective tissue was carefully peeled off. The isolated mouse spleen was transferred to another stainless steel mesh in a plate containing 10 ml of incomplete medium, and then ground into a cell suspension with a syringe needle core to allow the spleen cells to enter the incomplete medium in the plate. Pipetted several times with a pipette to yield a single cell suspension which was then counted. Usually $1 \times 10^8$-$2.5 \times 10^8$ spleen cells were obtained for each mouse. $1 \times 10^8$ spleen cells and $1 \times 10^7$ myeloma cells SP2/0 were fused by PEG treatment to prepare hybridomas, and plated into 96-well plates containing feeder cells. Hybridoma cells were cultivated and screened using HAT medium (a cell culture medium containing three substances: hypoxantin, aminopterin and thymidin). Hybridoma cells were observed under microscope for growth, and the cell culture supernatant was drawn for antibody detection when they grew to more than 1/10 of the well bottom area. The hybridoma cells in the positive antibody detection well were monoclonalized by a limiting dilution method, and the cell culture supernatant was drawn for antibody detection again when they grew to more than 1/10 of the well bottom area. A monoclonal hybridoma cell strain secreting an antibody having a high affinity to the rVAR2 recombinant protein was selected. Part of the cells was cryopreserved. Some of the remaining cells were further cultured to collect supernatant containing anti-rVAR2 monoclonal antibody. Some of the cells were used to extract RNA, and the variable region coding sequences of the heavy and light chains of the murine IgG antibody were subsequently analyzed with RT-PCR using specific primers. Among them, a cell strain secreting monoclonal antibody 5H4 was selected. The coding sequences of the variable regions of its heavy chain and light chain are shown in Table 1, the amino acid sequences of the variable regions of the heavy chain and light chain of 5H4 are shown in Table 2, and the complementary determining region (CDR) sequences of the heavy chain and light chain of 5H4 are shown in Table 3.

TABLE 1

Coding DNA sequence of heavy chain variable region ($V_H$) and light chain variable region ($V_L$) of monoclonal antibody 5H4

| Name | DNA sequence |
|---|---|
| $V_H$ chain of 5H4 (SEQ ID NO. 21) | GAGGTGAAGCTGGTGGAGTCTGGGGGAGGCTTAGTGAAG CCTGGAGGGTCCCTAAAACTCTCCTGTGCAGCCTCTGGA TTCACTTTCAGTAACTATGCCATGTCTTGGGTTCGCCAG TCTCCAGAGAGGAGGCTGGAGTGGGTCGCAGAAATTAGT ATTACTGGTCGTTACACCTACTATCCAGACACTGTGACG GGCCGATTCACCATCTCCAGAGACAATGCCAAGAACACC CTGTACCTGGAAATGAGCAGTCTGAGGTCTGAGGACACG GCCATGTATTATTGTACAAGGGAGGGATATGACTACGCC CCCTCCTGGTTTGCTTACTGGGGCCAAGGGACTCTGGTC ACTGTCTCTGCA |
| $V_L$ chain of 5H4 (SEQ ID NO. 22) | GATGTTGTGATGACCCAAACTCCACTCTCCCTGCCTGTC AGTCTTGGAGATCAAGCCTCCATCTCTTGCAGATCTGGT CAGACCCTTGTACATCGTAATGGAATCACCTATTTAGAA TGGTACCTGCAGAAACCAGGCCAGTCTCCAAAGCTCCTG ATCTACAAAGTTTCCAACCGATTTTCTGGAGTCCCAGAC AGGTTCAGTGGCAGTGGATCAGGGACAGATTTCACACTC AAGATCAGCAGAGTGGAGGCTGAGGATCTGGGAATTTAT TACTGCTTTCAAGGTTCACATGTTCCTCGGACGTTCGGT GGAGGCACCAAGCTGGAAATCAAA |

TABLE 2

Amino acid sequence of heavy chain variable region ($V_H$) and light chain variable region ($V_L$) of monoclonal antibody 5H4

| Name | Amino acid sequence |
|---|---|
| $V_H$ chain of 5H4 (SEQ ID NO. 19) | EVKLVESGGGLVKPGGSLKLSCAASGFTFSNYAMSWVRQ SPERRLEWVAEISITGRYTYYPDTVTGRFTISRDNAKNT LYLEMSSLRSEDTAMYYCTREGYDYAPSWFAYWGQGTLV TVSA |
| $V_L$ chain of 5H4 (SEQ ID NO. 20) | DVVMTQTPLSLPVSLGDQASISCRSGQTLVHRNGITYLE WYLQKPGQSPKLLIYKVSNRFSGVPDRFSGSGSGTDFTL KISRVEAEDLGIYYCFQGSHVPRTFGGGTKLEIK |

TABLE 3

Complementary determining region (CDR) sequence of heavy chain variable region (V$_H$) and light chain variable region (V$_L$) of monoclonal antibody 5H4

| Name | CDR1 | CDR2 | CDR3 |
| --- | --- | --- | --- |
| V$_H$ chain of 5H4 | GFTFSNYA (SEQ ID NO. 13) | ISITGRYT (SEQ ID NO. 14) | TREGYDYAPSWFAY (SEQ ID NO. 15) |
| V$_L$ chain of 5H4 | QTLVHRNGITY (SEQ ID NO. 16) | KVS (SEQ ID NO.17) | FQGSHVPRT (SEQ ID NO. 18) |

Example 3: Detection of Targetability of rVAR2 Protein to Tumor Cells Using Flow Cytometry 5×10$^5$ cells of different types of in vitro isolated or cultured (including normal cell control group and tumor cell group) were incubated with purified prokaryotically or eukaryotically expressed rVAR2 protein, and then murine polyclonal antibody against rVAR2 protein obtained by immunizing mice, and the purchased FITC dye-labeled goat anti-mouse secondary antibody (IgG H&L, Abcam, cat #ab6785) for 45 minutes, respectively. The cells were washed 3 times with a 4° C. pre-cooled PBS solution containing 0.02% NaN$_3$ and 2% FBS before incubated with the next reagent or after the reagent incubation was completed, with 2 min intervals. Finally, flow cytometry was used to detect the targetability of rVAR2 protein to several different types of tumor cells. The experimental groups are shown in Table 4 below:

TABLE 4

Experimental groups in detection of targetability of rVAR2 protein to tumor cells using flow cytometry

|  | rVAR2 protein (0.5 µM) | Mouse anti-rVAR2 polyclonal antibody | FITC-labeled goat anti-mouse secondary antibody (IgG H&L) |
| --- | --- | --- | --- |
| CTR1 | − | − | − |
| CTR2 | − | + | + |
| EXP1 | + | + | + |

The results are shown in FIG. 3. As can be seen from FIG. 3, rVAR2 protein can specifically target several different types of tumor cells. For example, human lung cancer cell lines, including NCI-H460 (large cell lung cancer cell line, ATCC #HTB177), NCI-H520 (squamous cell lung cancer cell line, ATCC #HTB182) and A549 (lung adenocarcinoma cell line, ATCC #CCL185) were specifically bound by rVAR2 protein to varying degrees. rVAR2 protein also could target and bind to human placental choriocarcinoma cell line BeWo (ATCC #CCL98). In addition, B-cell lymphoma cell line Raji (ATCC #CCL86) and acute bone marrow Leukemia cell line KG-1a (ATCC #CCL246.1) were also specifically bound by rVAR2 protein. However, the binding between rVAR2 protein and PBMC from healthy people, as well as the binding of rVAR2 protein to human umbilical vein endothelial cells (HUVEC, ATCC #PCS-100-010) were negative.

Example 4: Functional Verification of Murine Monoclonal Antibody 5H4 Against rVAR2 Recombinant Protein Western blot was used to verify the binding ability of monoclonal antibody 5H4 to its specific antigen of rVAR2 recombinant protein. The primary antibody was the purified monoclonal antibody 5H4, and the secondary antibody was HRP-labeled goat anti-mouse antibody. The results are shown in FIG. 4.

Figure 4:
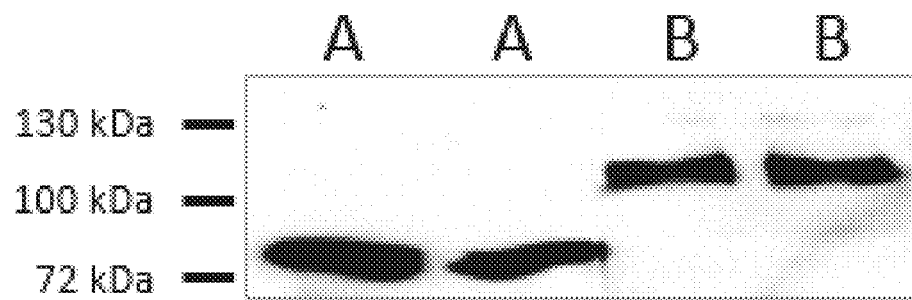
FIG. 4 shows identification of the binding effect of monoclonal antibody 5H4 to rVAR2 protein using Western blot, where A is the prokaryotically expressed and purified rVAR2 protein, and B is the eukaryotically expressed and purified rVAR2 protein.

It can be seen from FIG. 4 that the prokaryotically expressed and purified rVAR2 protein was about 74 kDa, and the eukaryotically expressed and purified rVAR2 protein was about 115 kDa. Western blot identification results showed that the monoclonal antibody 5H4 can bind to prokaryotically or eukaryotically expressed and purified rVAR2 protein.

Example 5: Screening of Epitope for Anti-rVAR2 Monoclonal Antibody 5H4

According to the structural and functional properties of rVAR2 which is the core domain responsible for binding between VAR2CSA and placental-like chondroitin sulfate A(pl-CSA), it can be subdivided into three main domain components, including ID1, DBL2X and ID2a (Clausen et al., 2012). The amino acid sequence of rVAR2 protein and its domain components are as follows:

The amino acid sequence of rVAR2 protein is as follows (SEQ ID NO.39):

NYIKGDPYFAEYATKLSFILNSSDANNPSEKIQKNNDEVCNCNESGIASV

EQEQISDPSSNKTCITHSSIKANKKKVCKHVKLGVRENDKDLRVCVIEHT

SLSGVENCCCQDFLRILQENCSDNKSGSSSNGSCNNKNQEACEKNLEKVL

ASLTNCYKCDKCKSEQSKKNNKNWIWKKSSGKEGGLQKEYANTIGLPPRT

QSLCLVVCLDEKGKKTQELKNIRTNSELLKEWIIAAFHEGKNLKPSHEKK

NDDNGKKLCKALEYSFADYGDLIKGTSIWDNEYTKDLELNLQKIFGKLFR

KYIKKNNTAEQDTSYSSLDELRESWWNTNKKYIWLAMKHGAGMNSTTCCG

DGSVTGSGSSCDDIPTIDLIPQYLRFLQEWVEHFCKQRQEKVKPVIENCK

SCKESGGTCNGECKTECKNKCEVYKKFIEDCKGGDGTAGSSWVKRWDQIY

KRYSKYIEDAKRNRKAGTKNCGPSSTTNAAENKCVQSDIDSFFKHLIDIG

LTTPSSYLSIVLDDNICGADKAPWTTYTTYTTTEKCNKETDKSKLQQCNT

AVVVNVPSPLGNTPHGYKYACQCKIPTNEETCDDRKEYMNQWSCGSARTM

KRGYKNDNYELCKYNGVDVKPTTVRSNSSKLD.

The amino acid sequence of ID1 polypeptide is as follows (SEQ ID NO. 2):

NYIKGDPYFAEYATKLSFILNSSDANNPSEKIQKNNDEVCNCNESGIASV

EQEQISDPSSNKTCITHSSIKANKKKVCKHVKLGVRENDKDLRVCVIEHT

SLSGVENCCCQDFLRILQENCSDNKSGSSSNGSCNNKNQEACEKNLEKVL

AS.

The amino acid sequence of DBL2X polypeptide is as follows (SEQ ID NO.3):

LTNCYKCDKCKSEQSKKNNKNWIWKKSSGKEGGLQKEYANTIGLPPRTQS

LCLVVCLDEKGKKTQELKNIRTNSELLKEWIIAAPFHEGKNLKPSHEKKND

DNGKKLCKALEYSFADYGDLIKGTSIWDNEYTKDLELNLQKIFGKLFRKY

IKKNNTAEQDTSYSSLDELRESWWNTNKKYIWLAMKHGAGMNSTTCCGDG

SVTGSGSSCDDIPTIDLIPQYLRFLQEWVEHFCKQRQEKVKPVIENCKSC

KESGGTCNGECKTECKNKCEVYKKFIEDCKGGDGTAGSSWVKRWDQIYKR

YSKYIEDAKRNRKAGTKNCGPSSTTNAAENKCVQSDIDSFFKHLIDIG.

The amino acid sequence of ID2a polypeptide is as follows (SEQ ID NO. 4):

LTTPSSYLSIVLDDNICGADKAPWTTYTTYTTTEKCNKETDKSKLQQCNT

AVVVNVPSPLGNTPHGYKYACQCKIPTNEETCDDRKEYMNQWSCGSARTM

KRGYKNDNYELCKYNGVDVKPTTVRSNSSKLD.

Figure 5:
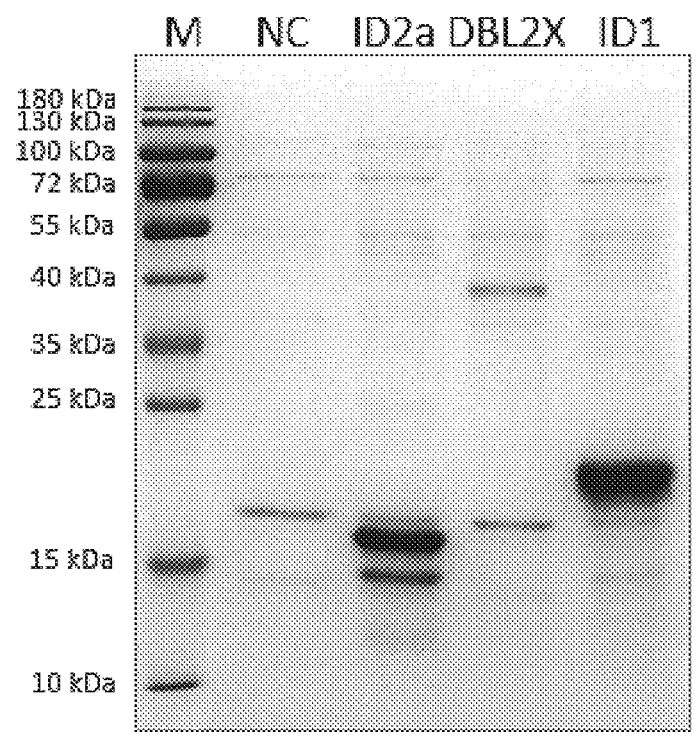
FIG. 5 shows 12% SDS-PAGE protein gel electrophoresis detection of prokaryotically expressed and purified ID1, DBL2X and ID2a polypeptides with Strep-tag protein tags, where M is the protein molecular weight standard; NC is the negative control, that is the lysate of E. coli transfected by empty vectors; ID2a is the purified ID2a protein with Strep-tag, DBL2X is the purified DBL2X protein with Strep-tag, and ID1 is the purified ID1 protein with Strep-tag.

The coding DNA sequences of ID1, DBL2X, and ID2a polypeptides were cloned into *E. coli* expression vectors. Proteins of the three were obtained after protein expression and purification. SDS-PAGE protein gel electrophoresis results are shown in FIG. 5. The purified ID2a protein with Strep-tag had a predicted average molecular weight of about 15 kDa; the purified DBL2X protein with Strep-tag had a predicted average molecular weight of 40 kDa; and the purified ID1 protein with Strep-tag a predicted average molecular weight of 17 kDa.

The epitope for anti-rVAR2 monoclonal antibody 5H4 was preliminarily identified using an antigen-specific ELISA: The purified 3 antigen peptides including ID1, DBL2X, and ID2a were diluted with $Na_2CO_3$—$NaHCO_3$ buffer (pH 9.6) to a final concentration of 1 μg/ml, respectively, added to 96-well microtiter plates at 100 μl antigen/well, and incubated at 37° C. for 2 h. Washed twice with PBS-T buffer (PBS buffer containing 0.05% (v/v) Tween 20, pH7. 4). The liquid in the wells of the microtiter plate was slapped to dry. 250 μl 5% (v/v) skim milk/PBS-T buffer was added to each well, and incubated at 37° C. for 1.5 h. Washed 4 times with PBS-T, and the liquid in the wells of the microtiter plate was slapped to dry. 100 μl of monoclonal antibody 5H4 (primary antibody) purified from the supernatant of the hybridoma diluted in 0.1% (v/v) skim milk/PBS-T buffer was added to each well, and incubated at 37° C. for 60 min. After incubating with the primary antibody, the plate was washed 4 times with PBS-T, and the liquid in the wells of the microtiter plate was slapped to dry. 100 μl of HRP-labeled goat anti-mouse IgG (secondary antibody) diluted with 0.1% (v/v) skim milk/PBS-T buffer at 1:8000 was added to each well, and incubated at 37° C. for 45 min. After incubating with the secondary antibody, the plate was washed 4 times with PBS-T, and the liquid in the wells of the microtiter plate was slapped to dry. 100 μl TMB chromogenic substrate was added to each well, the plate was then incubated at 37° C. under darkness for 10 min, and then 50 μl of 1 M sulfuric acid was added to each well to stop the reaction, and the absorbance of each well at 450 nm was measured.

Figure 6:
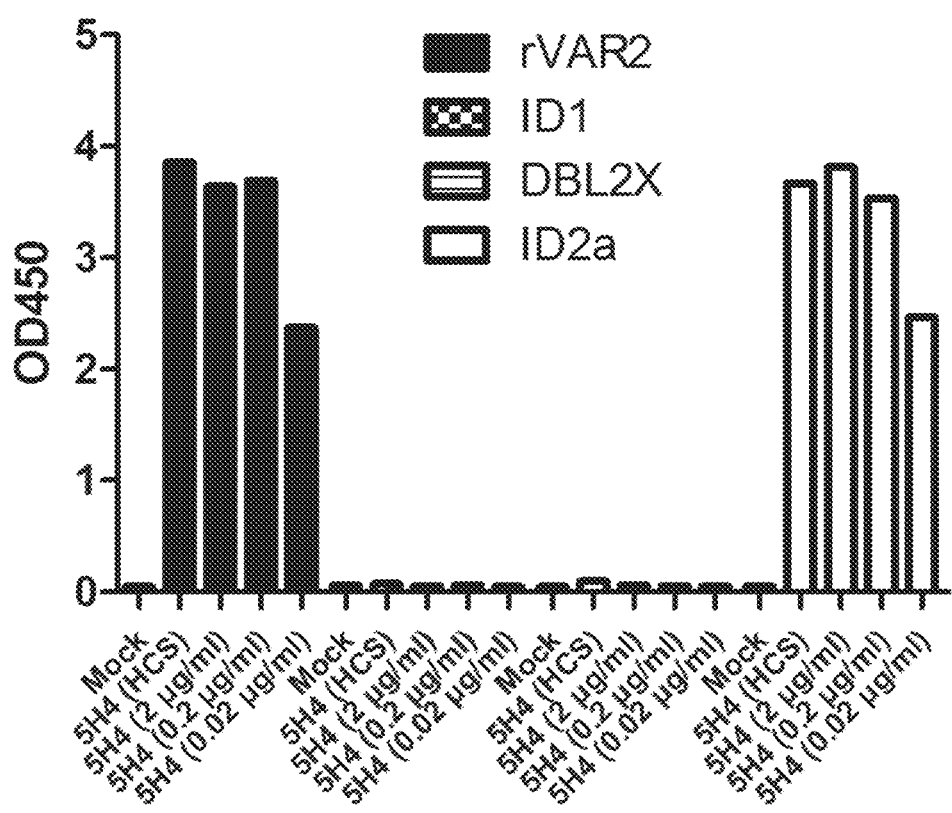
FIG. 6 shows the epitope screening for anti-rVAR2 monoclonal antibody 5H4, where Mock is the blank control, wherein the detection system was the same as the experimental group except that no monoclonal antibody 5H4 was added; and HCS is hybridoma cell supernatant, that is the supernatant expressed by mouse B cell hybridoma.

The ELISA results are shown in FIG. 6. Only the detection results of ID2a antigen peptide-coated wells are consistent with the detection results of rVAR2 protein-coated wells, indicating that the epitope of anti-rVAR2 monoclonal antibody 5H4 is located on the ID2a polypeptide epitope.

Example 6: Construction of CAR-T Cell and Functional Mechanism Thereof

Figure 7:
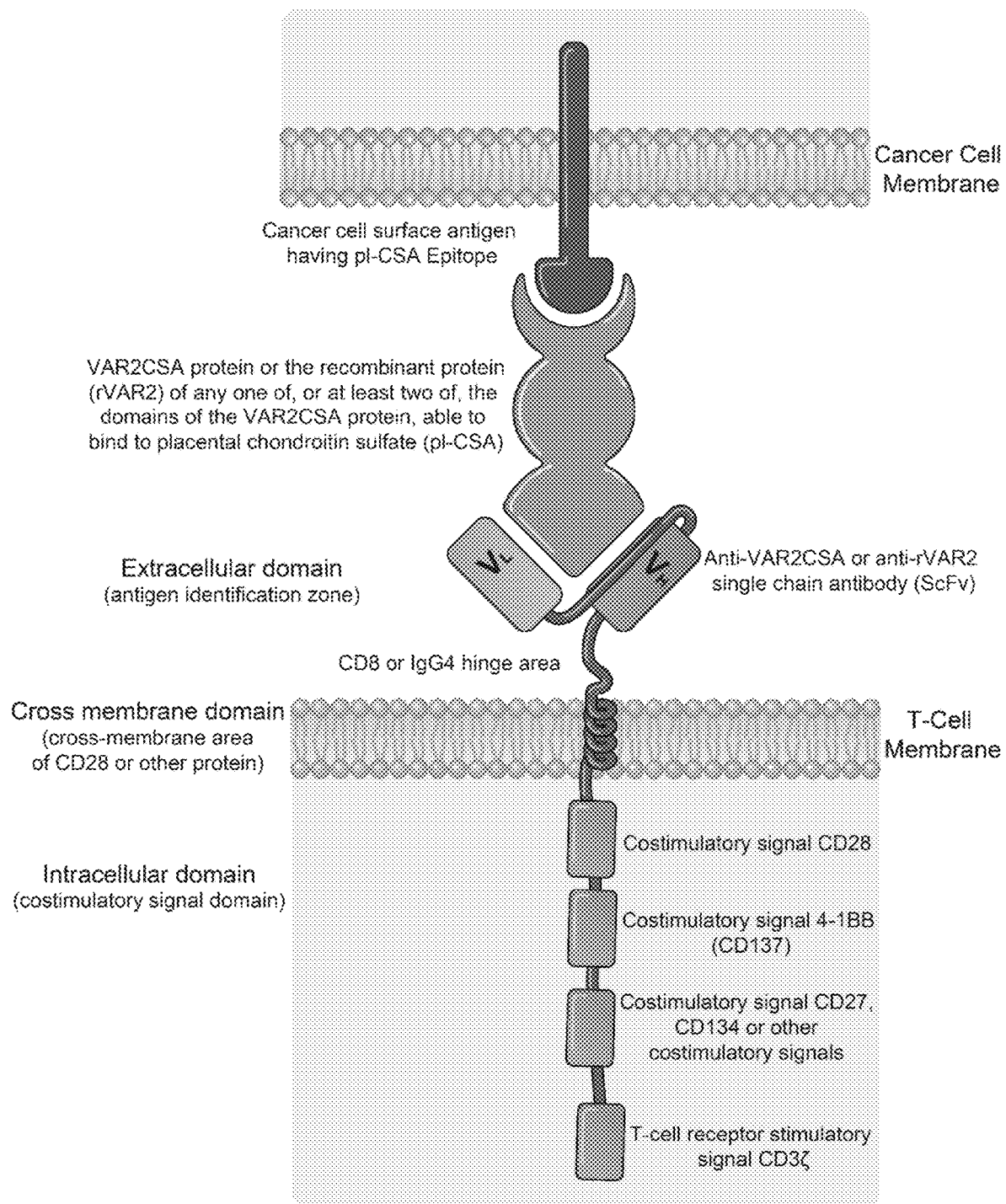
FIG. 7 (A) is a schematic diagram showing the binding mode among T cells expressing the chimeric antigen receptor of the present invention, VAR2CSA full-length protein (or its pl-CSA binding domain recombinant protein rVAR2), and tumor cells expressing pl-CSA epitope.
Figure 7:
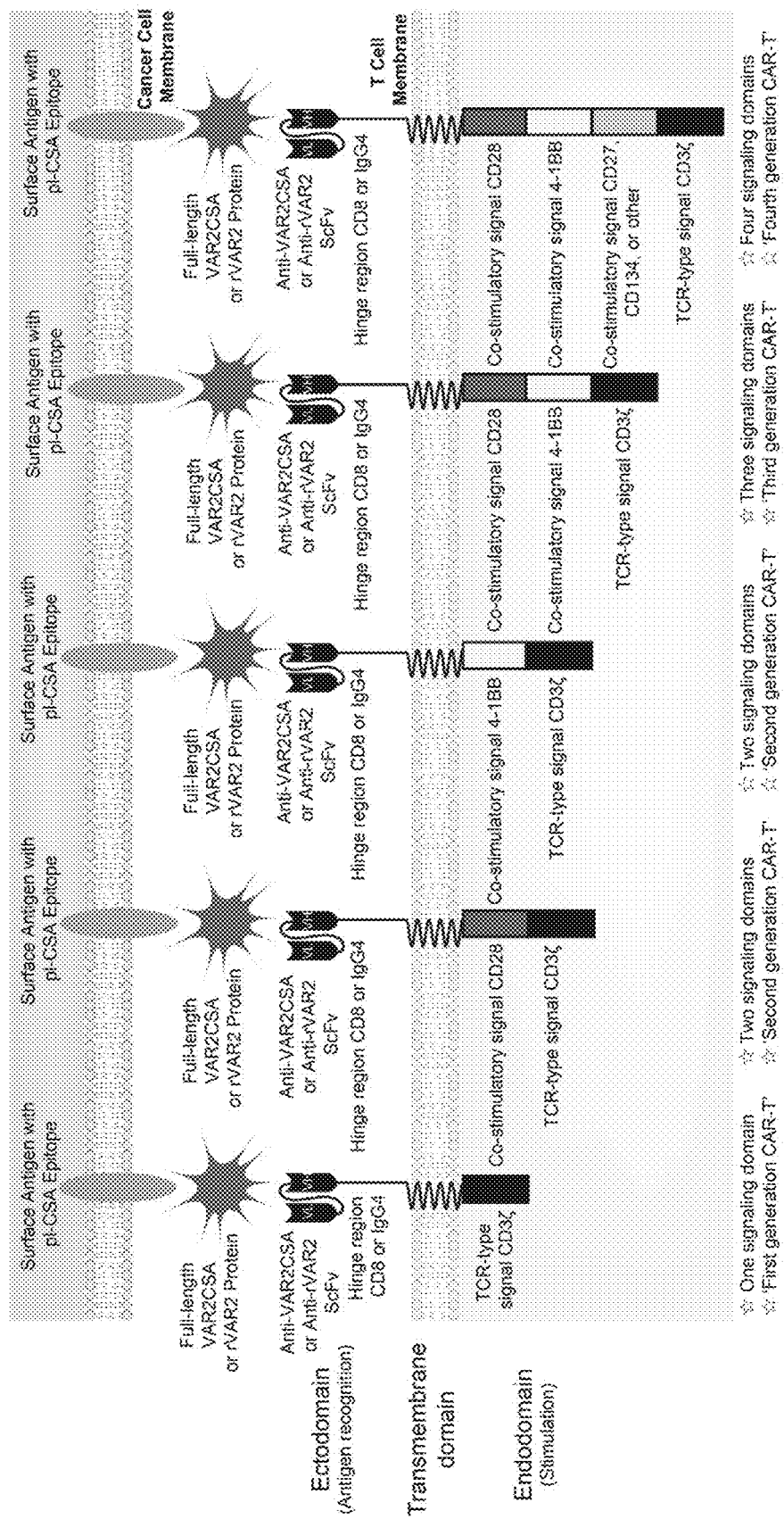

In order to further improve the killing activity of this broad-spectrum CAR-T cell based on VAR2CSA and enhance its application safety, a switchable CAR-T cell comprising VAR2CSA or its pl-CSA binding domain recombinant protein (rVAR2) and CAR-T (CART-anti-VAR2CSA or CART-anti-rVAR2) cell made of its single-chain antibody (anti-VAR2CSA ScFv or anti-rVAR2 ScFv) as a system was constructed: The full-length VAR2CSA protein or the rVAR2 protein was used to bind and mark tumor cells based on its targetability to tumor cells. Then, CART-anti-VAR2CSA or CART-anti-rVAR2 was constructed using murine single-chain antibody or humanized single-chain antibody that we developed and was specific for the full-length VAR2CSA protein or the rVAR2 protein. The mechanism of this system is to indirectly target and kill tumor cells marked by the full-length VAR2CSA protein or rVAR2 protein using CART-anti-VAR2CSA or CART-anti-rVAR2. A schematic diagram is shown in FIG. 7.

The switchable CAR-T cell technology system constructed by the VAR2CSA full-length protein or the recombinant protein of its pl-CSA binding domain together with CAR-T cells constructed with its single-chain antibody is named sCART-anti-VAR2CSA (a system containing the full-length protein of VAR2CSA) or sCART-anti-rVAR2 cell (a system containing recombinant protein of the pl-CSA binding domain of VAR2CSA protein).

Figure 8:
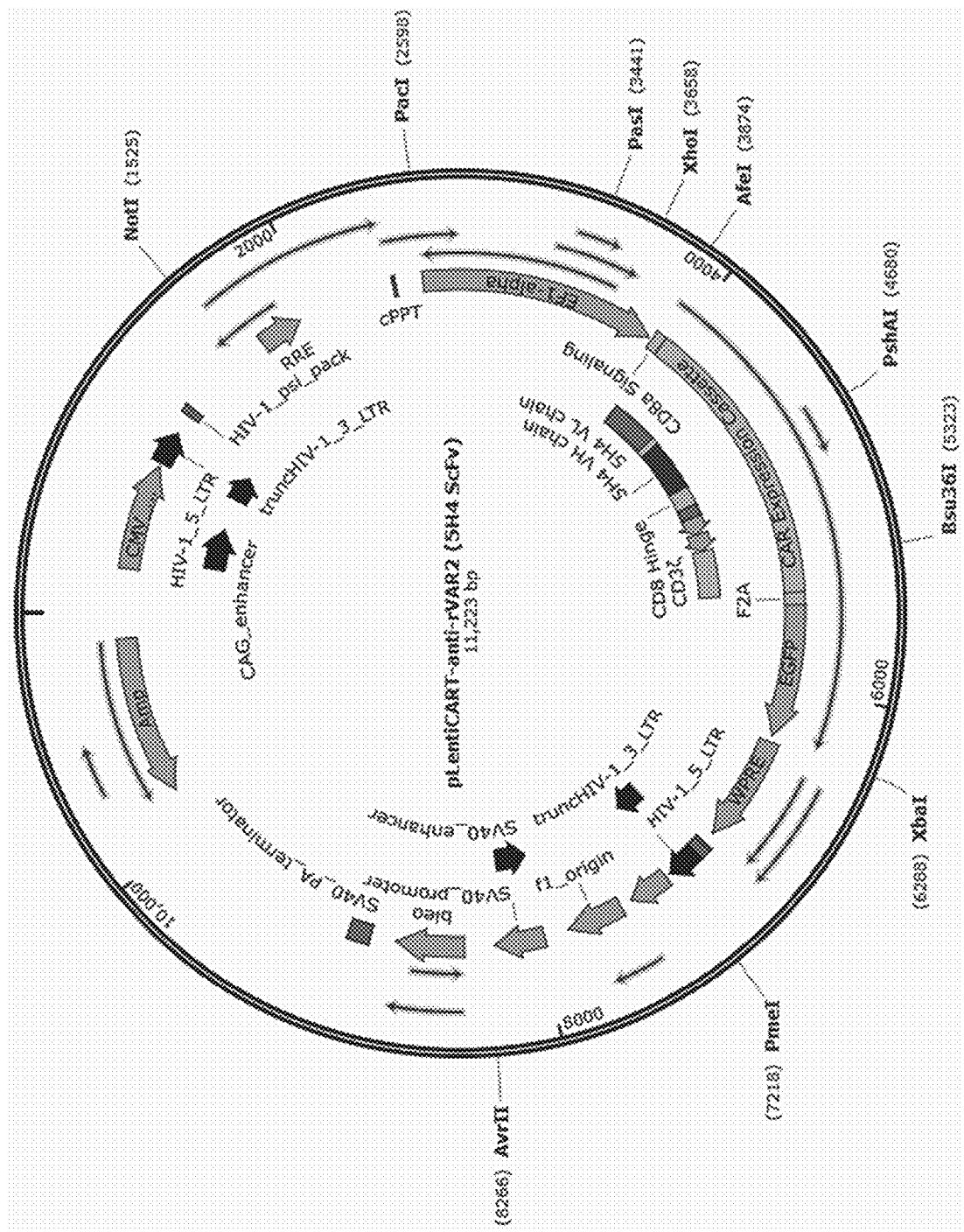
FIG. 8 is a plasmid map of the lentiviral expression vector of pLentiCART-anti-rVAR2 based on 5H4 single-chain antibody.

Taking CART-anti-rVAR2 (5H4 ScFv) as an example, as shown in FIG. 8, its single-chain antibody ScFv sequence responsible for recognizing the ID2a epitope on rVAR2 includes the $V_H$ chain of anti-rVAR2 monoclonal antibody 5H4 and the $V_L$ chain of 5H4 as well as the connecting sequence L (Linker) between the two, wherein the linker sequence includes but is not limited to amino acid sequences such as GGGGSGGGGSGGGGS.

Example 7: Detection of Stability of rVAR2 Protein in Human Serum

In order to confirm whether rVAR2 protein can be used as a navigation system of CART-anti-rVAR2 cells to target and kill tumor cells, it is first necessary to determine whether rVAR2 protein can stably exist in human blood.

Therefore, about 1 ml of serum was separated from 2 ml of blood donated by a patient with non-small cell lung cancer (male, age: 64). Then to each well of a V-bottom 96-well plate, 25 μl of patient's serum and 5 μl rVAR2 recombinant protein which was filtered and sterilized by a 0.2 μm protein low-adsorption filter membrane were added and mixed to a final concentration of the rVAR2 recombinant protein of 0.2 μg/μl. The plated was placed in a 37° C., 5% $CO_2$ incubator for processing.

Samples were collected according to the number of days the samples were placed in the incubator (Day). Day 0 means the 0th day, that is, 30 μl of sample was collected immediately after mixing. Day 1 means that 30 μl of sample that was processed for one day (24 h) in the 37° C., 5% $CO_2$ incubator was collected, and so on. Samples on Day 2, Day 3, Day 4, Day 5, Day 7, Day 9, Day 11, Day 14, Day 17 and Day 22 were collected. Each sample was added with 570 μl of SDS-PAGE protein loading buffer (2×), boiled for 3 min, cooled and stored at −20° C. for later use. For negative control group (NC), 10 µl of the lung cancer patient's serum was diluted to a total volume of 20 times with SDS-PAGE protein loading buffer (2×), boiled for 3 min, cooled and stored at −20° C. for later use. For positive control group (PC), the purified rVAR2 recombinant protein was diluted with SDS-PAGE protein loading buffer (2×) to 0.1 µg/µl, boiled for 3 minutes, cooled and stored at −20° C. for later use.

Samples were divided into two groups. 5 µl of the prepared samples were taken, respectively, and loaded on a 10% SDS-PAGE gel for electrophoresis. One group was transferred to a PVDF membrane, and the stability of rVAR2 recombinant protein with Strep-tag was detected through Western blot using an anti-Strep-tag monoclonal antibody.

Figure 9:
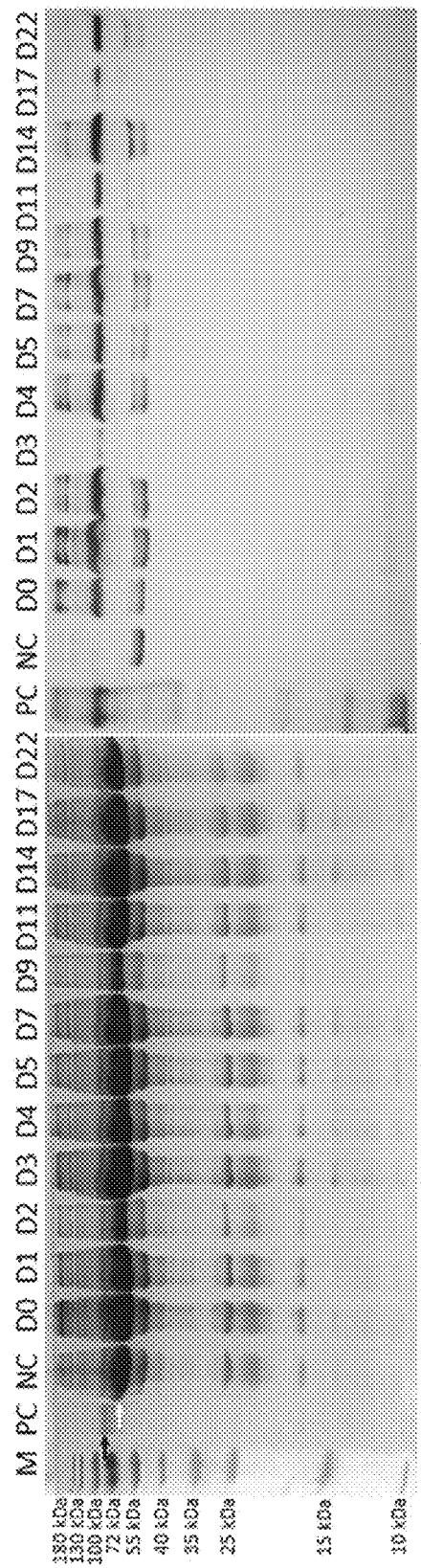
FIG. 9 (A) is 10% SDS-PAGE protein gel electrophoresis detection of the stability of rVAR2 recombinant protein in human serum.

The results are shown in FIG. 9 (A) and FIG. 9 (B). The rVAR2 recombinant protein with a Strep-tag has an average molecular weight of about 74 kDa, and human serum albumin has an average molecular weight of about 66.5 kDa, indicating that under treatment conditions of 37° C., 5% $CO_2$ incubator, rVAR2 recombinant protein can stably exist in the serum of lung cancer patients for more than 3 weeks.

Example 8: Construction of CART-Anti-rVAR2 Cells

First, the chimeric antigen receptor (CAR) expression vector of CART-anti-rVAR2 cells were constructed. The 5H4 ScFv of the anti-ID2a domain of the rVAR2 recombinant protein was cloned into a lentiviral expression vector, where the vector was sequentially cascaded, via the EF1α promoter downstream, with the CD8 signaling peptide, 5H4 ScFv, CD8a hinge region (CD8 Hinge), CD28 transmembrane sequence (TM), CD28 costimulatory factor, CD137 (4-1BB) costimulatory factor and CD3 domain sequence, as shown in FIG. 8.

The large amount of extracted CART-anti-rVAR2 (5H4 ScFv) expression plasmids were mixed with the third-generation lentiviral packaging plasmids pMDLg-pRRE:pRSV-Rev:pMD2.G with a mass ratio 3:1:1, and co-transfected to HEK293T cells by a PEI transfection method. After 72 h of transfection, the culture supernatant was collected, and then the collected culture supernatant was filtered by a 0.45 µm membrane filter, such filtered solutions were then concentrated by ultrafiltration to a lentivirus titer of $1.6 \times 10^8$ TU/ml to $1 \times 10^{10}$ TU/ml, and stored at −80° C. in the refrigerator for later use. The CART-anti-rVAR2 (5H4 ScFv) cells were produced according to the following steps.
(1) Isolation of PBMC Cells 50 ml of whole blood donated by a volunteer was centrifuged at 800 g for 10 min. A white cell layer was taken out and then diluted to 8 ml with 2% FBS (Fetal Bovine Serum) containing PBS buffer. 4 ml of LymphoPrep was pipetted into a 15 ml centrifuge tube, and then the diluted blood was gently added along the tube wall onto the layered solution, keeping the interface between the two solution layers clear. The resulting mixture was centrifuged at 800 g for 20 min (acceleration was set to 6 and deceleration was set to 1). Off-white mononuclear cells were gently pipetted with a Pasteur pipette, added to another centrifuge tube that already contained 10 ml of RF-10 (RPMI 1640 medium with 10% inactivated FBS), and then mixed well. The above resulting mixture was centrifuged at 500 g for 5 min, and the supernatant was discarded. After that, the cells were resuspended by adding 10 ml of RF-10, 20 microliters of cell suspension was stained with Trypan blue and counted. Then the cells were centrifuged at 350 g for 10 min, and the supernatant was discarded.

Figure 10:
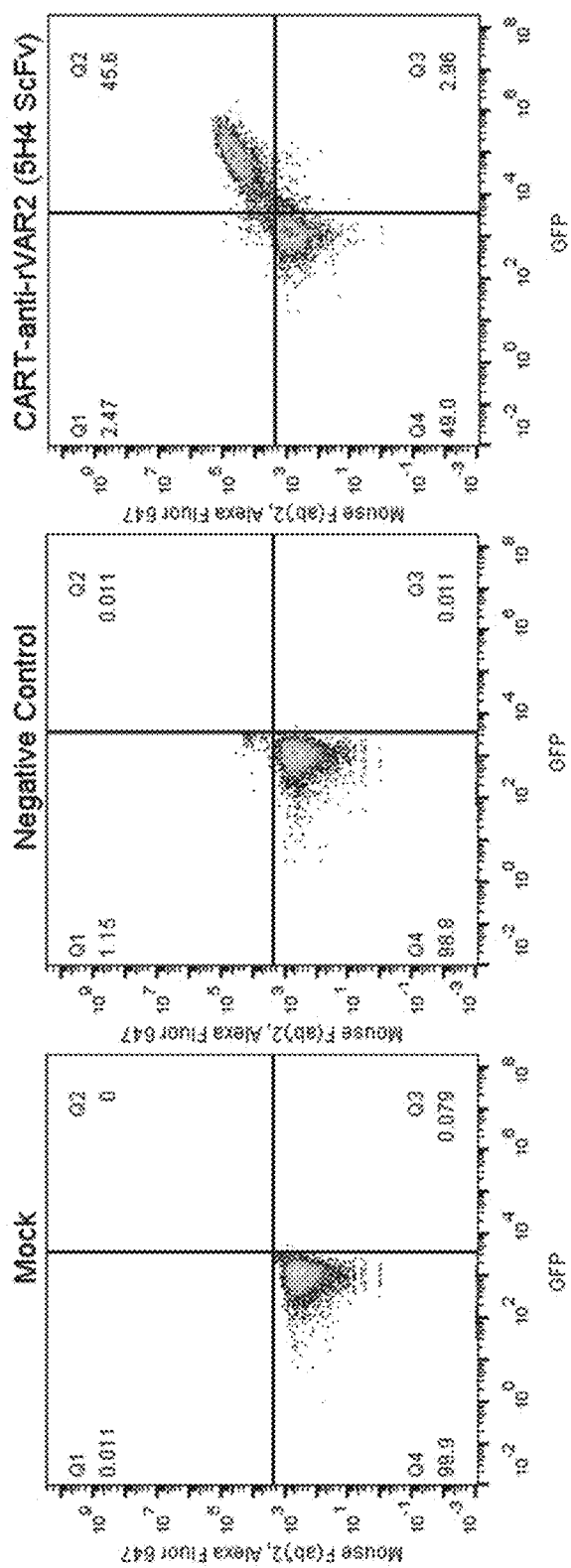
FIG. 10 shows the lentiviral transfection efficiency of CART-anti-rVAR2 (5H4 ScFv) cells by flow cytometry and their expression in the extracellular antigen recognition domain (5H4 ScFv), where Mock is a T-cell group alone, where T cells are not treated with Alexa Fluor 647-labeled goat-anti-mouse F(ab')2 IgG antibody, Negative Control is a negative control, where T cells are treated with Alexa Fluor 647-labeled goat-anti-mouse F(ab')2 IgG antibody, and CART-anti-rVAR2 (5H4 ScFv) is a CAR-T cell group that expresses a chimeric antigen receptor of CART-anti-rVAR2 (5H4 ScFv) and that is obtained after a lentiviral vector expressing the chimeric antigen receptor is transfected into T cells.

(2) Magnetic Activated Cell Sorting of $CD4^+$ T and $CD8^+$ T Cells $CD4^+$ T cells and $CD8^+$ T cells in PBMC were isolated respectively by using the Dynabeads® CD4 Positive Isolation Kit (Invitrogen, Cat. #11331D) and the Dynabeads® CD8 Positive Isolation Kit (Invitrogen, Cat. #11333D). The basic operation steps of the isolation were as follows. Magnetic beads (Dynabeads) were vortexed well for resuspension. 25 µl of Dynabeads was transferred to a tube and mixed well with 1 ml of added Buffer 1. Place the tube in a magnet for 1 min and discard the supernatant. 25 µl of Buffer 1 was added to suspend the magnetic beads for later use. PBMC cells were resuspended with Buffer 1 to a density of $1 \times 10^7$ cells/ml. 25 µl of washed Dynabeads CD4 was added to 1 ml of PBMC cells, incubated at 2 to 8° C. for 20 min, and placed on a shaker and rotated at an angle. The tube was placed on the magnet for 2 min, and the supernatant was collected. The tube was removed from the magnet, 1 ml of Buffer 1 was added into the tube and pipetted and mixed, the tube was placed back on the magnetic stand for 2 min, and the supernatant was collected; the above steps were repeated again, the supernatant containing other cells collected in the above steps was transferred to a new sterile tube for subsequent isolation of $CD8^+$ T cells. 100 µl Buffer 2 was added to resuspend the $CD4^+$ T cells combined by the magnetic beads, 10 µl of DETACHaBEAD was added, and the above mixture was incubated at room temperature for 45 min to release the cells from the Dynabeads. The tube was placed on the magnet for 1 min, and the supernatant containing the cells was transferred to a new tube. 500 µl of Buffer 2 was added to the new tube to wash the magnetic beads 2 to 3 times, and the supernatant containing part of $CD4^+$ T cells was collected. 4 ml of Buffer 2 was added and centrifuged at 350 g for 5 min, the supernatant containing DETACHaBEAD was removed, and the collected $CD4^+$ T cells were resuspended with Buffer 2. $CD8^+$ T cells were subsequently collected from the supernatant collected in the process of $CD4^+$ T cell sorting according to the operation instructions on the kit.
(3) Culture of T Cells $CD4^+$ T and $CD8^+$ T cells sorted by magnetic beads were centrifuged at 350 g for 10 min. The centrifuged cells were resuspended with RF-10 (RPMI 1640 medium containing 10% inactivated FBS) and counted. $CD4^+$ T and $CD8^+$ T cells were added at a ratio of 1:1 in a cell culture plate with a cell density of $5 \times 10^5$ cells/ml and cultured. CD3/CD28 antibody magnetic beads were added to a T-cell special medium, where a ratio of the quantity of added magnetic beads to the cells was 1:1. Recombinant human interleukin-2 (rhIL-2) was added to make the final concentration 10 ng/ml. The cells were counted 2 to 3 times a week, and the cell proliferation was recorded.
(4) Lentiviral Transfection of T Cells $CD4^+$ T and $CD8^+$ T cells sorted by magnetic beads were centrifuged at 350 g for 10 min. The centrifuged cells were resuspended with an added complete medium and then counted. $CD4^+$ T and $CD8^+$ T cells were added at a ratio of 1:1 in a 96-well plate and cultured with a cell density of $5 \times 10^5$ cells/ml and $1 \times 10^5$ cells per well. The magnetic beads were washed and added to a culture dish with a ratio of 1:1 to the cells. Recombinant human IL-2 (rhIL-2) was added to make the final concentration 10 µg/l. The cells were stimulated for 24 h and then infected. Polybrene was added to make the final concentration 6 µg/ml. The above mixture was mixed well. 16 to 24 h later, the medium was changed. After 3 days, the T cell infection efficiency was detected by flow cytometry. The results are shown in FIG. 10. It can be seen that the infection efficiency detected by flow cytometry was about 45%, which can make the preparation of CAR-T cells more efficiently.

Example 9: Cytokine Secretion Detection in the Process of the Co-Incubation of Switchable CAR-T Cells, sCART-Anti-rVAR2 System, with Tumor Cells In order to detect whether switchable CAR-T cells, sCART-anti-rVAR2 system, had a potential killing effect on tumor cells, first, the cytokine secretion level in the process of the co-incubation of the sCART-anti-rVAR2 system with tumor cells was detected by using the relevant cytokine detection kit [R&D Systems, Human IFN-γ ELISA detection kit (Cat. #dif50) and Human IL-2 ELISA detection kit (Cat. #d2050)] according to the following steps.
(1) Collection and Pretreatment of Cells
Effector cells [CAR-T cells: CART-anti-rVAR2 (5H4 ScFv)] and target cells (cancer cells) were collected separately and centrifuged at 250×g for 4 min, and the supernatant was removed. The cells were washed with 10 ml of serum-free 1640 medium twice, and then the cell density was adjusted with the 1640 medium to $6 \times 10^5$ cells/ml.
(2) Experimental Grouping
Experimental group: effector cells [CART-anti-rVAR2 (5H4 ScFv), CARTV2] and target cells (Raji, R) were evenly spread in a 48-well plate at a ratio of 1:1, where each type of cells was set to $1.25 \times 10^5$/well/250 that is, the total volume was 500 where in the pre-coincubation group of effector cells (or target cells) and rVAR2 recombinant proteins (rVAR2, V), rVAR2 proteins and effector cells (or target cells) were incubated at 37° C. for 1 h before subsequent operations. The above groups were respectively marked as: [CARTV2+V]+R, which means that effector cells were first co-incubated with rVAR2 recombinant proteins, and then the target cells were added; or [V+R]+CARTV2, which means that rVAR2 recombinant proteins were first co-incubated with the target cells, and then effector cells were added. In this experiment, the concentration of rVAR2 recombinant proteins used herein was 18 nM.
Control group: T+R group, namely the group of normal T Cells (T) plus target cells, where each cell was set to $1.25 \times 10^5$ cells/well/250 the insufficient part was made up with 250 μl of RPMI-1640 culture medium, and the total volume was kept at 500 μl;
CARTV2+R group, namely the group of effector cells plus target cells;
[T+V]+R group, that is, normal T cells were co-incubated with rVAR2 recombinant proteins, and then added to a target cell group; and
[V+R]+T group, that is, rVAR2 recombinant proteins were co-incubated with target cells, and then added to a normal T cell group;
where after cells in each group were incubated at 37° C. in an incubator for 24 h, the supernatant was collected for detection.
(3) Detection of Cytokines
1) 100 μl of Assay Diluent was added to each well of the ELISA plate.
2) Samples and the concentration-gradient-diluted standards were added to the ELISA well plate that had been coated with antibody, with 100 μl per well, and incubated at room temperature for 2 h after air bubbles were removed.
3) The liquid in the well was removed, 300 μl of rinsing buffer was added to each well to wash the mixture in the well three times, and the rinsing buffer was bolted up at the last time of washing.
4) 200 μl of corresponding detection antibody was added and incubated for 2 h at room temperature.
5) Step 3) was repeated.
6) 200 μl of substrate solution (A+B) was added and incubated for 30 min at room temperature in the dark.
7) 50 μl of stop solution was added, and the solution would change from blue to yellow (if the color was green or the color was not changed, tap it to mix well).
8) The absorbance was detected at 450 nm by using a microplate reader.
9) The sample concentration was calculated based on the standard curve.

Figure 11:
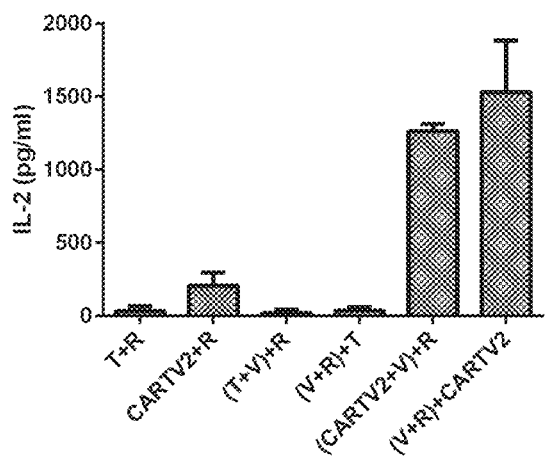
FIG. 11 (A) shows the detection of secretion levels of IL-2 in the process of incubation of sCART-anti-rVAR2 (5H4 ScFv) system with Raji cells.
Figure 11:
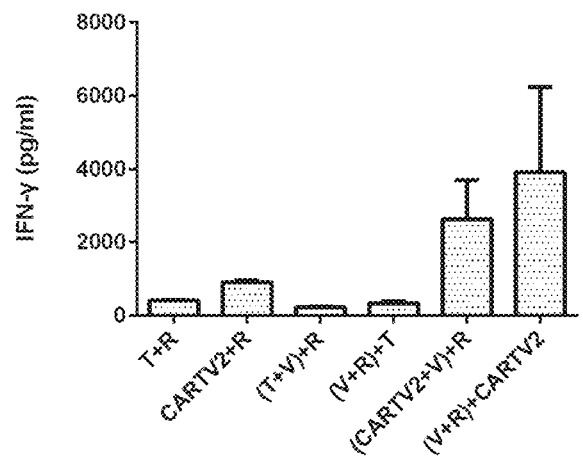

The detection results are shown in FIG. 11 (A) and FIG. 11 (B). As shown in the above figures, a large amount of IFN-γ and IL-2 were secreted in the process of the co-incubation of sCART-anti-rVAR2 system with the tumor cell of B-cell lymphoma cell line Raji (ATCC #CCL86) or the co-incubation of sCART-anti-rVAR2 system with the large cell lung cancer cell line (NCI-H460, ATCC #HTB177), which improves anti-tumor activity, and also indicates that the sCART-anti-rVAR2 system has a potential killing effect on different types of tumor cells.

Example 10: Validation of Killing Effects of Switchable CAR-T Cells, sCART-Anti-rVAR2 System, on Tumor Cells by a Far Red Method First, the target cells were labeled by the Far Red method, namely, the CellTrace™ Far Red Cell Proliferation Kit (Invitrogen, Cat. #C34564) was used for labeling of the target cells. (1) An appropriate amount of tumor cells were taken and centrifuged at 300×g for 3 min, and the supernatant was removed. (2) After the cells were resuspended with PBS buffer, the cells were centrifuged at 300×g for 3 min, the supernatant was removed, and this step was repeated once. (3) The cells were resuspended with PBS buffer to a cell density of $1 \times 10^6$ cells/ml. (4) 1 μl of Far-Red at a concentration of 200 μM was added to each 1 ml of cells, and incubated in a water bath at 37° C. for 20 min. (6) After the incubation, 5 times volume of RF-10 medium (RPMI 1640 medium containing 10% inactivated FBS) was added to stop the reaction in 5 min. (7) The cells were centrifuged at 300 g for 3 min, and the supernatant was removed. (8) The cells were resuspended to $5 \times 10^5$/ml with the T cell expansion medium.

Then, CAR-T cells were taken and centrifuged at 300×g for 3 min, and then the supernatant was removed; after the cells were resuspended with PBS buffer, the cells were centrifuged at 300×g for 3 min, and the supernatant was removed, and the above steps were repeated once; and the cells were resuspended to a density of $5 \times 10^5$ cells/ml with the T cell expansion medium (Gibco, Cat. #A10485).

In order to validate the ability of effector cells [CAR-T cells: CART-anti-rVAR2 (5H4 ScFv)] to kill target cells (cancer cells Raji) under the navigation of rVAR2 recombinant protein, the experiment was divided into the following groups, specifically as shown in Table 5. In each group, no matter which cell the rVAR2 recombinant proteins were co-incubated with first, the molar concentration of the proteins was 500 times that of the co-incubated corresponding cells, and the ratio of effector cells and target cells was 2:1.

TABLE 5

Experimental grouping for detection of killing effects of sCART-anti-rVAR2
(5H4 ScFv) system on tumor cells by the Far Red method

| Group | Full name | Note |
|---|---|---|
| V + R | rVAR2 + Raji | rVAR2 recombinant proteins were incubated with Raji cells in an incubator at 37° C. with 5% $CO_2$. |
| [T + V] + R | [T cells + rVAR2] + Raji | Normal T cells were co-incubated with rVAR2 recombinant proteins in an incubator at 37° C. with 5% $CO_2$ for 30 min, and then added to Raji cells to co-incubate. |
| [V + R] + T | [rVAR2 + Raji] + T cells | rVAR2 recombinant proteins were co-incubated with Raji cells in an incubator at 37° C. with 5% $CO_2$ for 30 min, and then added to normal T cells to co-incubate. |
| CART19 + R | CART-CD19+ + Raji | CAR-T cells constructed based on the single chain fragment variable antibody (ScFv) of the CD19 antigen were co-incubated with Raji cells in an incubator at 37° C. with 5% $CO_2$, as the positive control. |
| [CARTV2 + V] + R | [CART-anti-rVAR2 (5H4 ScFv) + rVAR2] + Raji | CART-anti-rVAR2 (5H4 ScFv) cells were co-incubated with rVAR2 recombinant proteins in an incubator at 37° C. with 5% $CO_2$ for 30 min, and then added to Raji cells to co-incubate. |
| [V + R] + CARTV2 | [rVAR2 + Raji] + CART-anti-rVAR2 (5H4 ScFv) | rVAR2 recombinant proteins were co-incubated with Raji cells in an incubator at 37° C. with 5% $CO_2$ for 30 min, and then added to CART-anti-rVAR2 (5H4 ScFv) cells to co-incubate. |

After 16 h of incubation in the incubator at 37° C. with 5% $CO_2$, the cells were centrifuged at 300 g for 3 min and then collected; the centrifuged cells were washed twice with PBS buffer containing 2% inactivated FBS and 0.02% $NaN_3$, and then the cells were resuspended with the PBS buffer; and the Far-Red fluorescence signals were detected by flow cytometry (excitation wavelength of 630 nm and emission wavelength of 661 nm).

Figure 12:
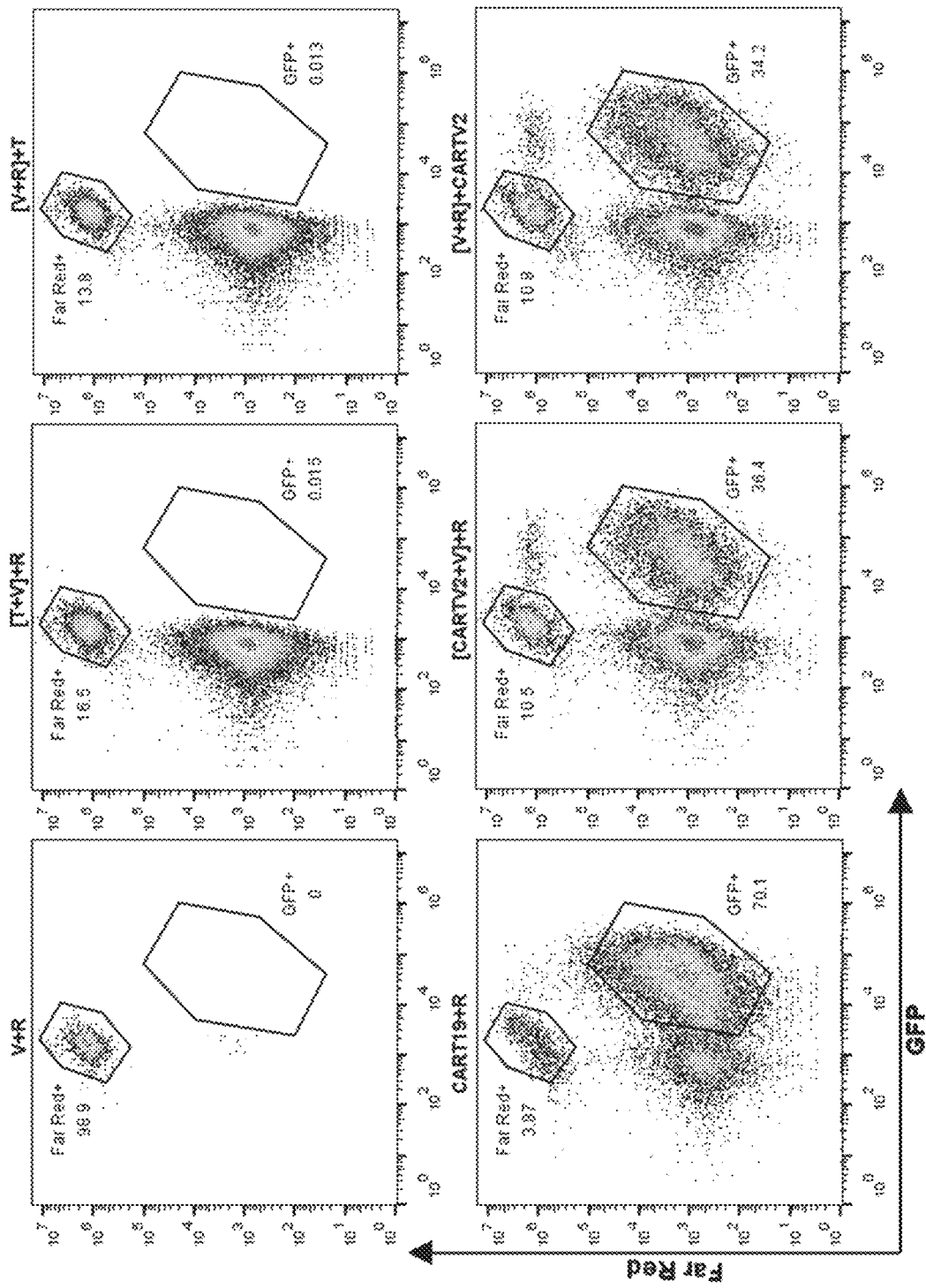
FIG. 12 shows the detection of the in-vitro ability of sCART-anti-rVAR2 (5H4 ScFv) system to kill tumor cells Raji, where the signal in the Far Red+ gate indicates the proportion of Raji cells, and the signal in the GFP+ gate indicates the proportion of CART-anti-rVAR2 (5H4 ScFv) cells.

The results of in vitro experiments are shown in FIG. 12, and the results indicate that the sCART-anti-rVAR2 (5H4 ScFv) system had killing effects on Raji cells, and as long as in the presence of rVAR2 recombinant proteins and T cells, it had a certain killing effect on Raji cells, from which it is speculated that normal T cells can also recognize and kill target cells labeled with rVAR2 recombinant protein.

Example 11: In-Vitro Real-Time Dynamic Monitoring of Killing Effects of Switchable CAR-T Cells, sCART-Anti-rVAR2 System, on Tumor Cells First, the target cells Raji were stained and labeled by using the same Far-Red method as in Example 10, and then the Raji cells were resuspended with the corresponding T cell culture medium and plated into a 96-well culture plate at a density of 5000 cells/100 μl per well. The prepared CART-anti-rVAR2 (5H4 ScFv) cells were added at the effector-target ratio of 4:1. Since the lentiviral transfection efficiency was about 45% or more, the effector-target ratio as from 2:1 to 4:1. Two groups were divided according to the order of adding the rVAR2 recombinant proteins as the navigator between the effector cells and target cells: the rVAR2 recombinant proteins were co-incubated with CART-anti-rVAR2 cells (the final concentration of rVAR2 recombinant proteins was 18 nM, and CART-anti-rVAR2 cells were at a density of 20,000 cells/100 μl) at 37° C. for 1 h and then added to tumor cells, and this group was named [CART-anti-rVAR2 (5H4 ScFv)+rVAR2]+Raji group; or rVAR2 recombinant proteins (the final concentration of rVAR2 recombinant proteins was 18 nM as well) were co-incubated with Raji cells at 37° C. for 1 h, and then added to CART-anti-rVAR2 cells at a density of 20,000 cells/100 μl, and this group was named [Raji+rVAR2]+CART-anti-rVAR2 (5H4 ScFv) group. In addition, since Raji is a B cell lymphoma cell line with high cell surface expression of CD19, CD19-targeting CAR-T cells (CART-CD19[+] cells, Porter et al., *N Engl J Med.* 2011, 365 (8): 725-33; Grupp et al., *N Engl J Med.* 2013; 368 (16): 1509-18.) could be used as positive control to measure the effects of the sCART-anti-rVAR2 (5H4 ScFv) system, so CART-CD19[+]+Raji with the same cell number and effector-target ratio was set as a positive control group.

All experimental groups and control groups were placed in the incubator and cultured at 37° C. with 5% $CO_2$, and the killing activity of sCART-anti-rVAR2 (5H4 ScFv) system on tumor cells was observed in real time by the JuLI Stage automated live cell imaging system.

Figure 13:
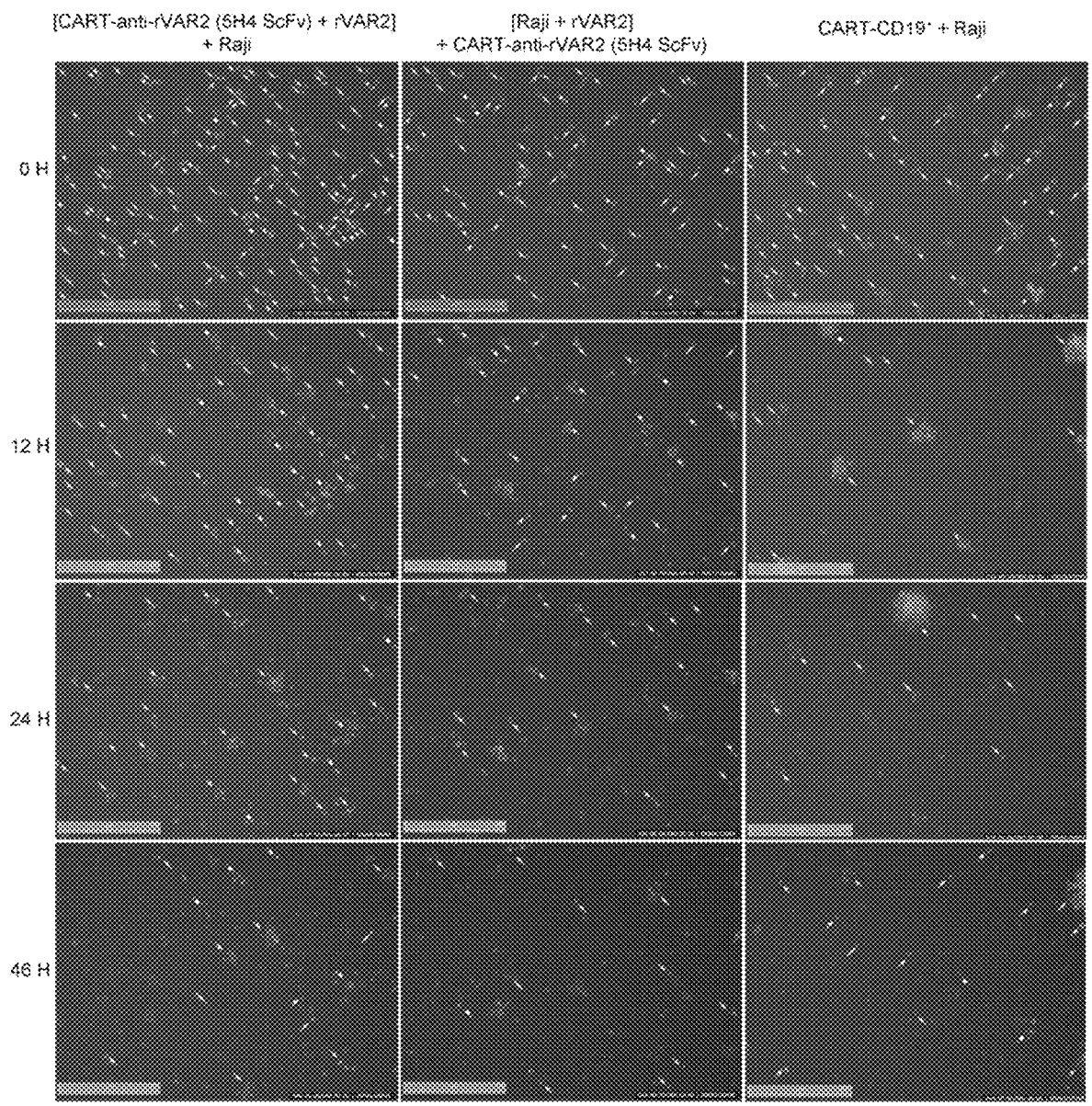
FIG. 13 shows the in-vitro real-time dynamic monitoring of killing effects of sCART-anti-rVAR2 (5H4 ScFv) system on Raji cells, where cells marked by white arrows are tumor cells Raji labeled by Far Red, and cells not marked are CART-anti-rVAR2 (5H4 ScFv) cells co-expressing the GFP reporter gene.

The results are shown in FIG. 13. The results indicate that the switch-mediated CAR-T cell system of sCART-anti-rVAR2 (5H4 ScFv) had significant in-vitro killing effects on the tumor cells Raji, but the killing effects required longer time than CART-CD19[+], which indicates that its killing effect was milder, and it may help to reduce the toxic side effects of CAR-T cells and enhance the safety of CAR-T cells.

The applicant has stated that although the detailed method of the present invention is described through the embodiments described above, the present invention is not limited to the detailed method described above, which means that implementation of the present invention does not necessarily depend on the detailed method described above. It should be apparent to those skilled in the art that any improvements made to the present invention, equivalent replacements of various raw materials of the product, the addition of adjuvant ingredients, and the selection of specific manners, etc. in the present invention all fall within the protection scope and the scope of disclosure of the present invention.

The invention claimed is:

1. A chimeric antigen receptor, wherein the chimeric antigen receptor contains an antigen recognition domain,
wherein the antigen recognition domain is a domain which recognizes a malarial protein VAR2CSA or a recombinant protein comprising any one or at least two placental-like chondroitin sulfate A-binding domains of the malarial protein VAR2CSA,
wherein the antigen recognition domain contains a variable heavy chain and a variable light chain,
wherein
the variable heavy chain comprises:
CDR1 having an amino acid sequence as shown in SEQ ID NO. 13;
CDR2 having an amino acid sequence as shown in SEQ ID NO. 14; and
CDR3 having an amino acid sequence as shown in SEQ ID NO. 15;
and
the variable light chain comprises:
CDR1 having an amino acid sequence as shown in SEQ ID NO. 16;
CDR2 having an amino acid sequence as shown in SEQ ID NO. 17; and
CDR3 having an amino acid sequence as shown in SEQ ID NO. 18.

2. The chimeric antigen receptor according to claim 1, wherein the antigen recognition domain recognizes an ID2a epitope of the VAR2CSA,
wherein the ID2a contains an amino acid sequence as shown in SEQ ID NO. 4.

3. The chimeric antigen receptor according to claim 1, wherein the variable heavy chain contains an amino acid sequence as shown in SEQ ID NO. 19 or an amino acid sequence having at least 90% amino acid sequence homology to the amino acid sequence as shown in SEQ ID NO. 19; and
the variable light chain contains an amino acid sequence as shown in SEQ ID NO. 20 or an amino acid sequence having at least 90% amino acid sequence homology to the amino acid sequence as shown in SEQ ID NO. 20.

4. The chimeric antigen receptor according to claim 1, wherein the chimeric antigen receptor further comprises any one of, or a combination of at least two of, a hinge region, a transmembrane domain and an intracellular costimulatory signal region;
wherein, the hinge region is a human CD8a hinge region;
the transmembrane domain is a human CD28 transmembrane domain; and
the intracellular signal region is any one of, or a combination of at least two of, a human CD27 intracellular signal region, a human CD134 intracellular signal region, a human CD28 intracellular signal region, or a human 4-1BB intracellular signal region.

5. The chimeric antigen receptor according to claim 1 for transfecting and expanding CAR-T cells.

6. A cell system, comprising:
an immune effector cell expressing the chimeric antigen receptor according to claim 1; and
a malarial protein VAR2CSA, or a recombinant protein comprising any one or at least two placental-like chondroitin sulfate A-binding domains of the malarial protein VAR2CSA.

7. The cell system according to claim 6, wherein the immune effector cell is any one of a T cell, a B cell, an NK cell, an NKT cell, a dendritic cell or macrophage.

8. A pharmaceutical composition, comprising the cell system according to claim 6, and pharmaceutically acceptable excipients.

* * * * *

SEQUENCE LISTING

<160> NUMBER OF SEQ ID NOS: 37

<210> SEQ ID NO 1
<211> LENGTH: 325
<212> TYPE: PRT
<213> ORGANISM: Artificial Sequence
<220> FEATURE:
<223> OTHER INFORMATION: DBL1X

<400> SEQUENCE: 1

```
Ser Gly Thr Asn Asp Pro Cys Asp Arg Ile Pro Pro Tyr Gly Asp
1               5                   10                  15

Asn Asp Gln Trp Lys Cys Ala Ile Ile Leu Ser Lys Val Ser Glu Lys
            20                  25                  30

Pro Glu Asn Val Phe Val Pro Arg Arg Gln Arg Met Cys Ile Asn
        35                  40                  45

Asn Leu Glu Lys Leu Asn Val Asp Lys Ile Arg Asp Lys His Ala Phe
50                  55                  60

Leu Ala Asp Val Leu Leu Thr Ala Arg Asn Glu Gly Glu Arg Ile Val
65                  70                  75                  80

Gln Asn His Pro Asp Thr Asn Ser Ser Asn Val Cys Asn Ala Leu Glu
                85                  90                  95

Arg Ser Phe Ala Asp Ile Ala Asp Ile Ile Arg Gly Thr Asp Leu Trp
                100                 105                 110

Lys Gly Thr Asn Ser Asn Leu Glu Gln Asn Leu Lys Gln Met Phe Ala
            115                 120                 125

Lys Ile Arg Glu Asn Asp Lys Val Leu Gln Asp Lys Tyr Pro Lys Asp
        130                 135                 140

Gln Asn Tyr Arg Lys Leu Arg Glu Asp Trp Trp Asn Ala Asn Arg Gln
145                 150                 155                 160

Lys Val Trp Glu Val Ile Thr Cys Gly Ala Arg Ser Asn Asp Leu Leu
                165                 170                 175

Ile Lys Arg Gly Trp Arg Thr Ser Gly Lys Ser Asn Gly Asp Asn Lys
                180                 185                 190

Leu Glu Leu Cys Arg Lys Cys Gly His Tyr Glu Glu Lys Val Pro Thr
            195                 200                 205

Lys Leu Asp Tyr Val Pro Gln Phe Leu Arg Trp Leu Thr Glu Trp Ile
        210                 215                 220

Glu Asp Phe Tyr Arg Glu Lys Gln Asn Leu Ile Asp Asp Met Glu Arg
225                 230                 235                 240

His Arg Glu Glu Cys Thr Ser Glu Asp His Lys Ser Lys Glu Gly Thr
                245                 250                 255

Ser Tyr Cys Ser Thr Cys Lys Asp Lys Cys Lys Lys Tyr Cys Glu Cys
                260                 265                 270

Val Lys Lys Trp Lys Ser Glu Trp Glu Asn Gln Lys Asn Lys Tyr Thr
            275                 280                 285

Glu Leu Tyr Gln Gln Asn Lys Asn Glu Thr Ser Gln Lys Asn Thr Ser
        290                 295                 300

Arg Tyr Asp Asp Tyr Val Lys Asp Phe Phe Lys Lys Leu Glu Ala Asn
305                 310                 315                 320

Tyr Ser Ser Leu Glu
                325
```

<210> SEQ ID NO 2
<211> LENGTH: 152
<212> TYPE: PRT

```
<213> ORGANISM: Artificial Sequence
<220> FEATURE:
<223> OTHER INFORMATION: ID1

<400> SEQUENCE: 2

Asn Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Pro Ser Glu Lys Ile
                20                  25                  30

Gln Lys Asn Asn Asp Glu Val Cys Asn Cys Asn Glu Ser Gly Ile Ala
            35                  40                  45

Ser Val Glu Gln Glu Gln Ile Ser Asp Pro Ser Ser Asn Lys Thr Cys
    50                  55                  60

Ile Thr His Ser Ser Ile Lys Ala Asn Lys Lys Val Cys Lys His
65                  70                  75                  80

Val Lys Leu Gly Val Arg Glu Asn Asp Lys Asp Leu Arg Val Cys Val
                85                  90                  95

Ile Glu His Thr Ser Leu Ser Gly Val Glu Asn Cys Cys Cys Gln Asp
                100                 105                 110

Phe Leu Arg Ile Leu Gln Glu Asn Cys Ser Asp Asn Lys Ser Gly Ser
            115                 120                 125

Ser Ser Asn Gly Ser Cys Asn Asn Lys Asn Gln Glu Ala Cys Glu Lys
    130                 135                 140

Asn Leu Glu Lys Val Leu Ala Ser
145                 150

<210> SEQ ID NO 3
<211> LENGTH: 348
<212> TYPE: PRT
<213> ORGANISM: Artificial Sequence
<220> FEATURE:
<223> OTHER INFORMATION: DBL2X

<400> SEQUENCE: 3

Leu Thr Asn Cys Tyr Lys Cys Asp Lys Cys Lys Ser Glu Gln Ser Lys
1               5                   10                  15

Lys Asn Asn Lys Asn Trp Ile Trp Lys Ser Ser Gly Lys Glu Gly
                20                  25                  30

Gly Leu Gln Lys Glu Tyr Ala Asn Thr Ile Gly Leu Pro Pro Arg Thr
            35                  40                  45

Gln Ser Leu Cys Leu Val Val Cys Leu Asp Glu Lys Gly Lys Lys Thr
    50                  55                  60

Gln Glu Leu Lys Asn Ile Arg Thr Asn Ser Glu Leu Leu Lys Glu Trp
65                  70                  75                  80

Ile Ile Ala Ala Phe His Glu Gly Lys Asn Leu Lys Pro Ser His Glu
                85                  90                  95

Lys Lys Asn Asp Asp Asn Gly Lys Lys Leu Cys Lys Ala Leu Glu Tyr
                100                 105                 110

Ser Phe Ala Asp Tyr Gly Asp Leu Ile Lys Gly Thr Ser Ile Trp Asp
            115                 120                 125

Asn Glu Tyr Thr Lys Asp Leu Glu Leu Asn Leu Gln Lys Ile Phe Gly
    130                 135                 140

Lys Leu Phe Arg Lys Tyr Ile Lys Lys Asn Asn Thr Ala Glu Gln Asp
145                 150                 155                 160

Thr Ser Tyr Ser Ser Leu Asp Glu Leu Arg Glu Ser Trp Trp Asn Thr
                165                 170                 175
```

-continued

```
Asn Lys Lys Tyr Ile Trp Leu Ala Met Lys His Gly Ala Gly Met Asn
            180                 185                 190
Ser Thr Thr Cys Cys Gly Asp Gly Ser Val Thr Gly Ser Gly Ser Ser
        195                 200                 205
Cys Asp Asp Ile Pro Thr Ile Asp Leu Ile Pro Gln Tyr Leu Arg Phe
210                 215                 220
Leu Gln Glu Trp Val Glu His Phe Cys Lys Gln Arg Gln Glu Lys Val
225                 230                 235                 240
Lys Pro Val Ile Glu Asn Cys Lys Ser Cys Lys Glu Ser Gly Gly Thr
                245                 250                 255
Cys Asn Gly Glu Cys Lys Thr Glu Cys Lys Asn Lys Cys Glu Val Tyr
            260                 265                 270
Lys Lys Phe Ile Glu Asp Cys Lys Gly Gly Asp Gly Thr Ala Gly Ser
        275                 280                 285
Ser Trp Val Lys Arg Trp Asp Gln Ile Tyr Lys Arg Tyr Ser Lys Tyr
290                 295                 300
Ile Glu Asp Ala Lys Arg Asn Arg Lys Ala Gly Thr Lys Asn Cys Gly
305                 310                 315                 320
Pro Ser Thr Thr Asn Ala Ala Glu Asn Lys Cys Val Gln Ser Asp
                325                 330                 335
Ile Asp Ser Phe Phe Lys His Leu Ile Asp Ile Gly
            340                 345
```

<210> SEQ ID NO 4
<211> LENGTH: 132
<212> TYPE: PRT
<213> ORGANISM: Artificial Sequence
<220> FEATURE:
<223> OTHER INFORMATION: ID2a

<400> SEQUENCE: 4

```
Leu Thr Thr Pro Ser Ser Tyr Leu Ser Ile Val Leu Asp Asp Asn Ile
1               5                   10                  15
Cys Gly Ala Asp Lys Ala Pro Trp Thr Thr Tyr Thr Thr Tyr Thr Thr
            20                  25                  30
Thr Glu Lys Cys Asn Lys Glu Thr Asp Lys Ser Lys Leu Gln Gln Cys
        35                  40                  45
Asn Thr Ala Val Val Val Asn Val Pro Ser Pro Leu Gly Asn Thr Pro
    50                  55                  60
His Gly Tyr Lys Tyr Ala Cys Gln Cys Lys Ile Pro Thr Asn Glu Glu
65                  70                  75                  80
Thr Cys Asp Asp Arg Lys Glu Tyr Met Asn Gln Trp Ser Cys Gly Ser
                85                  90                  95
Ala Arg Thr Met Lys Arg Gly Tyr Lys Asn Asp Asn Tyr Glu Leu Cys
            100                 105                 110
Lys Tyr Asn Gly Val Asp Val Lys Pro Thr Thr Val Arg Ser Asn Ser
        115                 120                 125
Ser Lys Leu Asp
    130
```

<210> SEQ ID NO 5
<211> LENGTH: 193
<212> TYPE: PRT
<213> ORGANISM: Artificial Sequence
<220> FEATURE:
<223> OTHER INFORMATION: ID2b

<400> SEQUENCE: 5

Asp Lys Asp Val Thr Phe Phe Asn Leu Phe Glu Gln Trp Asn Lys Glu
1               5                   10                  15

Ile Gln Tyr Gln Ile Glu Gln Tyr Met Thr Asn Thr Lys Ile Ser Cys
            20                  25                  30

Asn Asn Glu Lys Asn Val Leu Ser Arg Val Ser Asp Glu Ala Ala Gln
        35                  40                  45

Pro Lys Phe Ser Asp Asn Glu Arg Asp Arg Asn Ser Ile Thr His Glu
    50                  55                  60

Asp Lys Asn Cys Lys Glu Lys Cys Lys Cys Tyr Ser Leu Trp Ile Glu
65                  70                  75                  80

Lys Ile Asn Asp Gln Trp Asp Lys Gln Lys Asp Asn Tyr Asn Lys Phe
                85                  90                  95

Gln Arg Lys Gln Ile Tyr Asp Ala Asn Lys Gly Ser Gln Asn Lys Lys
            100                 105                 110

Val Val Ser Leu Ser Asn Phe Leu Phe Phe Ser Cys Trp Glu Glu Tyr
        115                 120                 125

Ile Gln Lys Tyr Phe Asn Gly Asp Trp Ser Lys Ile Lys Asn Ile Gly
    130                 135                 140

Ser Asp Thr Phe Glu Phe Leu Ile Lys Lys Cys Gly Asn Asp Ser Gly
145                 150                 155                 160

Asp Gly Glu Thr Ile Phe Ser Glu Lys Leu Asn Asn Ala Glu Lys Lys
                165                 170                 175

Cys Lys Glu Asn Glu Ser Thr Asn Asn Lys Met Lys Ser Ser Glu Thr
            180                 185                 190

Ser

<210> SEQ ID NO 6
<211> LENGTH: 368
<212> TYPE: PRT
<213> ORGANISM: Artificial Sequence
<220> FEATURE:
<223> OTHER INFORMATION: DBL3X

<400> SEQUENCE: 6

Cys Asp Cys Ser Glu Pro Ile Tyr Ile Arg Gly Cys Gln Pro Lys Ile
1               5                   10                  15

Tyr Asp Gly Lys Ile Phe Pro Gly Lys Gly Glu Lys Gln Trp Ile
            20                  25                  30

Cys Lys Asp Thr Ile Ile His Gly Asp Thr Asn Gly Ala Cys Ile Pro
            35                  40                  45

Pro Arg Thr Gln Asn Leu Cys Val Gly Glu Leu Trp Asp Lys Arg Tyr
    50                  55                  60

Gly Gly Arg Ser Asn Ile Lys Asn Asp Thr Lys Glu Ser Leu Lys Gln
65                  70                  75                  80

Lys Ile Lys Asn Ala Ile Gln Lys Glu Thr Glu Leu Leu Tyr Glu Tyr
                85                  90                  95

His Asp Lys Gly Thr Ala Ile Ile Ser Arg Asn Pro Met Lys Gly Gln
            100                 105                 110

Lys Glu Lys Glu Glu Lys Asn Asn Asp Ser Asn Gly Leu Pro Lys Gly
        115                 120                 125

Phe Cys His Ala Val Gln Arg Ser Phe Ile Asp Tyr Lys Asn Met Ile
    130                 135                 140

```
Leu Gly Thr Ser Val Asn Ile Tyr Glu Tyr Ile Gly Lys Leu Gln Glu
145                 150                 155                 160

Asp Ile Lys Lys Ile Ile Glu Lys Gly Thr Thr Lys Gln Asn Gly Lys
                165                 170                 175

Thr Val Gly Ser Gly Ala Glu Asn Val Asn Ala Trp Trp Lys Gly Ile
            180                 185                 190

Glu Gly Glu Met Trp Asp Ala Val Arg Cys Ala Ile Thr Lys Ile Asn
        195                 200                 205

Lys Lys Gln Lys Lys Asn Gly Thr Phe Ser Ile Asp Glu Cys Gly Ile
    210                 215                 220

Phe Pro Pro Thr Gly Asn Asp Glu Asp Gln Ser Val Ser Trp Phe Lys
225                 230                 235                 240

Glu Trp Ser Glu Gln Phe Cys Ile Glu Arg Leu Gln Tyr Glu Lys Asn
                245                 250                 255

Ile Arg Asp Ala Cys Thr Asn Asn Gly Gln Gly Asp Lys Ile Gln Gly
            260                 265                 270

Asp Cys Lys Arg Lys Cys Glu Glu Tyr Lys Lys Tyr Ile Ser Glu Lys
        275                 280                 285

Lys Gln Glu Trp Asp Lys Gln Lys Thr Lys Tyr Glu Asn Lys Tyr Val
    290                 295                 300

Gly Lys Ser Ala Ser Asp Leu Leu Lys Glu Asn Tyr Pro Glu Cys Ile
305                 310                 315                 320

Ser Ala Asn Phe Asp Phe Ile Phe Asn Asp Asn Ile Glu Tyr Lys Thr
                325                 330                 335

Tyr Tyr Pro Tyr Gly Asp Tyr Ser Ser Ile Cys Ser Cys Glu Gln Val
            340                 345                 350

Lys Tyr Tyr Glu Tyr Asn Asn Ala Glu Lys Lys Asn Asn Lys Ser Leu
        355                 360                 365

<210> SEQ ID NO 7
<211> LENGTH: 18
<212> TYPE: PRT
<213> ORGANISM: Artificial Sequence
<220> FEATURE:
<223> OTHER INFORMATION: ID3

<400> SEQUENCE: 7

Cys His Glu Lys Gly Asn Asp Arg Thr Trp Ser Lys Lys Tyr Ile Lys
1               5                   10                  15

Lys Leu

<210> SEQ ID NO 8
<211> LENGTH: 310
<212> TYPE: PRT
<213> ORGANISM: Artificial Sequence
<220> FEATURE:
<223> OTHER INFORMATION: DBL4epsilon

<400> SEQUENCE: 8

Glu Asn Gly Arg Thr Leu Glu Gly Val Tyr Val Pro Pro Arg Arg Gln
1               5                   10                  15

Gln Leu Cys Leu Tyr Glu Leu Phe Pro Ile Ile Lys Asn Lys Asn
                20                  25                  30

Asp Ile Thr Asn Ala Lys Lys Glu Leu Leu Glu Thr Leu Gln Ile Val
            35                  40                  45

Ala Glu Arg Glu Ala Tyr Tyr Leu Trp Lys Gln Tyr His Ala His Asn
        50                  55                  60
```

```
Asp Thr Thr Tyr Leu Ala His Lys Lys Ala Cys Cys Ala Ile Arg Gly
 65                  70                  75                  80

Ser Phe Tyr Asp Leu Glu Asp Ile Ile Lys Gly Asn Asp Leu Val His
                 85                  90                  95

Asp Glu Tyr Thr Lys Tyr Ile Asp Ser Lys Leu Asn Glu Ile Phe Asp
                100                 105                 110

Ser Ser Asn Lys Asn Asp Ile Glu Thr Lys Arg Ala Arg Thr Asp Trp
                115                 120                 125

Trp Glu Asn Glu Ala Ile Ala Val Pro Asn Ile Thr Gly Ala Asn Lys
130                 135                 140

Ser Asp Pro Lys Thr Ile Arg Gln Leu Val Trp Asp Ala Met Gln Ser
145                 150                 155                 160

Gly Val Arg Lys Ala Ile Asp Glu Lys Glu Lys Lys Lys Pro Asn
                165                 170                 175

Glu Asn Phe Pro Pro Cys Met Gly Val Gln His Ile Gly Ile Ala Lys
                180                 185                 190

Pro Gln Phe Ile Arg Trp Leu Glu Glu Trp Thr Asn Glu Phe Cys Glu
                195                 200                 205

Lys Tyr Thr Lys Tyr Phe Glu Asp Met Lys Ser Asn Cys Asn Leu Arg
210                 215                 220

Lys Gly Ala Asp Asp Cys Asp Asp Asn Ser Asn Ile Glu Cys Lys Lys
225                 230                 235                 240

Ala Cys Ala Asn Tyr Thr Asn Trp Leu Asn Pro Lys Arg Ile Glu Trp
                245                 250                 255

Asn Gly Met Ser Asn Tyr Asn Lys Ile Tyr Arg Lys Ser Asn Lys
                260                 265                 270

Glu Ser Glu Asp Gly Lys Asp Tyr Ser Met Ile Met Glu Pro Thr Val
                275                 280                 285

Ile Asp Tyr Leu Asn Lys Arg Cys Asn Gly Glu Ile Asn Gly Asn Tyr
                290                 295                 300

Ile Cys Cys Ser Cys Lys
305                 310

<210> SEQ ID NO 9
<211> LENGTH: 85
<212> TYPE: PRT
<213> ORGANISM: Artificial Sequence
<220> FEATURE:
<223> OTHER INFORMATION: ID4

<400> SEQUENCE: 9

Asn Ile Gly Glu Asn Ser Thr Ser Gly Thr Val Asn Lys Lys Leu Gln
1               5                   10                  15

Lys Lys Glu Thr Gln Cys Glu Asp Asn Lys Gly Pro Leu Asp Leu Met
                20                  25                  30

Asn Lys Val Leu Asn Lys Met Asp Pro Lys Tyr Ser Glu His Lys Met
                35                  40                  45

Lys Cys Thr Glu Val Tyr Leu Glu His Val Glu Gln Leu Lys Glu
                50                  55                  60

Ile Asp Asn Ala Ile Lys Asp Tyr Lys Leu Tyr Pro Leu Asp Arg Cys
65                  70                  75                  80

Phe Asp Asp Lys Ser
                85

<210> SEQ ID NO 10
```

<211> LENGTH: 298
<212> TYPE: PRT
<213> ORGANISM: Artificial Sequence
<220> FEATURE:
<223> OTHER INFORMATION: DBL5epsilon

<400> SEQUENCE: 10

Lys Met Lys Val Cys Asp Leu Ile Gly Asp Ala Ile Gly Cys Lys His
1               5                   10                  15

Lys Thr Lys Leu Asp Glu Leu Asp Glu Trp Asn Asp Val Asp Met Arg
            20                  25                  30

Asp Pro Tyr Asn Lys Tyr Lys Gly Val Leu Ile Pro Pro Arg Arg Arg
        35                  40                  45

Gln Leu Cys Phe Ser Arg Ile Val Arg Gly Pro Ala Asn Leu Arg Asn
    50                  55                  60

Leu Lys Glu Phe Lys Glu Glu Ile Leu Lys Gly Ala Gln Ser Glu Gly
65                  70                  75                  80

Lys Phe Leu Gly Asn Tyr Tyr Asn Glu Asp Lys Asp Lys Glu Lys Ala
                85                  90                  95

Leu Glu Ala Met Lys Asn Ser Phe Tyr Asp Tyr Glu Tyr Ile Ile Lys
            100                 105                 110

Gly Ser Asp Met Leu Thr Asn Ile Gln Phe Lys Asp Ile Lys Arg Lys
        115                 120                 125

Leu Asp Arg Leu Leu Glu Lys Glu Thr Asn Asn Thr Glu Lys Val Asp
130                 135                 140

Asp Trp Trp Glu Thr Asn Lys Lys Ser Ile Trp Asn Ala Met Leu Cys
145                 150                 155                 160

Gly Tyr Lys Lys Ser Gly Asn Lys Ile Ile Asp Pro Ser Trp Cys Thr
                165                 170                 175

Ile Pro Thr Thr Glu Thr Pro Pro Gln Phe Leu Arg Trp Ile Lys Glu
            180                 185                 190

Trp Gly Thr Asn Val Cys Ile Gln Lys Glu His Lys Glu Tyr Val
        195                 200                 205

Lys Ser Lys Cys Ser Asn Val Thr Asn Leu Gly Ala Gln Glu Ser Glu
210                 215                 220

Ser Lys Asn Cys Thr Ser Glu Ile Lys Lys Tyr Gln Glu Trp Ser Arg
225                 230                 235                 240

Lys Arg Ser Ile Gln Trp Glu Ala Ile Ser Glu Gly Tyr Lys Lys Tyr
                245                 250                 255

Lys Gly Met Asp Glu Phe Lys Asn Thr Phe Lys Asn Ile Lys Glu Pro
            260                 265                 270

Asp Ala Asn Glu Pro Asn Ala Asn Glu Tyr Leu Lys Lys His Cys Ser
        275                 280                 285

Lys Cys Pro Cys Gly Phe Asn Asp Met Gln
    290                 295

<210> SEQ ID NO 11
<211> LENGTH: 68
<212> TYPE: PRT
<213> ORGANISM: Artificial Sequence
<220> FEATURE:
<223> OTHER INFORMATION: ID5

<400> SEQUENCE: 11

Glu Ile Thr Lys Tyr Thr Asn Ile Gly Asn Glu Ala Phe Lys Gln Ile
1               5                   10                  15

```
Lys Glu Gln Val Asp Ile Pro Ala Glu Leu Glu Asp Val Ile Tyr Arg
             20                  25                  30

Leu Lys His His Glu Tyr Asp Lys Gly Asn Asp Tyr Ile Cys Asn Lys
         35                  40                  45

Tyr Lys Asn Ile Asn Val Asn Met Lys Lys Asn Asn Asp Asp Thr Trp
 50                  55                  60

Thr Asp Leu Val
 65
```

<210> SEQ ID NO 12
<211> LENGTH: 274
<212> TYPE: PRT
<213> ORGANISM: Artificial Sequence
<220> FEATURE:
<223> OTHER INFORMATION: DBL6epsilon

<400> SEQUENCE: 12

```
Lys Asn Ser Ser Asp Ile Asn Lys Gly Val Leu Leu Pro Pro Arg Arg
 1               5                  10                  15

Lys Asn Leu Phe Leu Lys Ile Asp Glu Ser Asp Ile Cys Lys Tyr Lys
             20                  25                  30

Arg Asp Pro Lys Leu Phe Lys Asp Phe Ile Tyr Ser Ala Ile Ser
         35                  40                  45

Glu Val Glu Arg Leu Lys Lys Val Tyr Gly Ala Lys Thr Lys Val
 50                  55                  60

Val His Ala Met Lys Tyr Ser Phe Ala Asp Ile Gly Ser Ile Ile Lys
 65                  70                  75                  80

Gly Asp Asp Met Met Glu Asn Asn Ser Ser Asp Lys Ile Gly Lys Ile
                 85                  90                  95

Leu Gly Asp Gly Val Gly Gln Asn Glu Lys Arg Lys Lys Trp Trp Asp
            100                 105                 110

Met Asn Lys Tyr His Ile Trp Glu Ser Met Leu Cys Gly Tyr Lys His
        115                 120                 125

Ala Tyr Gly Asn Ile Ser Glu Asn Asp Arg Lys Met Leu Asp Ile Pro
    130                 135                 140

Asn Asn Asp Asp Glu His Gln Phe Leu Arg Trp Phe Gln Glu Trp Thr
145                 150                 155                 160

Glu Asn Phe Cys Thr Lys Arg Asn Glu Leu Tyr Glu Asn Met Val Thr
                165                 170                 175

Ala Cys Asn Ser Ala Lys Cys Ser Thr Ser Asn Gly Ser Val Asp Lys
            180                 185                 190

Lys Glu Cys Thr Glu Ala Cys Lys Asn Tyr Ser Asn Phe Ile Leu Ile
        195                 200                 205

Lys Lys Lys Glu Tyr Gln Ser Leu Asn Ser Gln Tyr Asp Met Asn Tyr
    210                 215                 220

Lys Glu Thr Lys Ala Glu Lys Glu Ser Pro Glu Tyr Phe Lys Asp
225                 230                 235                 240

Lys Cys Asn Gly Glu Cys Ser Cys Leu Ser Glu Tyr Phe Lys Asp Glu
                245                 250                 255

Thr Arg Trp Lys Asn Pro Tyr Glu Thr Leu Asp Asp Thr Glu Val Lys
            260                 265                 270

Asn Asn
```

<210> SEQ ID NO 13
<211> LENGTH: 8

```
<212> TYPE: PRT
<213> ORGANISM: Artificial Sequence
<220> FEATURE:
<223> OTHER INFORMATION: CDR1

<400> SEQUENCE: 13

Gly Phe Thr Phe Ser Asn Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: CDR2

<400> SEQUENCE: 14

Ile Ser Ile Thr Gly Arg Tyr Thr
1               5

<210> SEQ ID NO 15
<211> LENGTH: 14
<212> TYPE: PRT
<213> ORGANISM: Artificial Sequence
<220> FEATURE:
<223> OTHER INFORMATION: CDR3

<400> SEQUENCE: 15

Thr Arg Glu Gly Tyr Asp Tyr Ala Pro Ser Trp Phe Ala Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDR1

<400> SEQUENCE: 16

Gln Thr Leu Val His Arg Asn Gly Ile Thr Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: CDR2

<400> SEQUENCE: 17

Lys Val Ser
1

<210> SEQ ID NO 18
<211> LENGTH: 9
<212> TYPE: PRT
<213> ORGANISM: Artificial Sequence
<220> FEATURE:
<223> OTHER INFORMATION: CDR3

<400> SEQUENCE: 18

Phe Gln Gly Ser His Val Pro Arg Thr
1               5

<210> SEQ ID NO 19
<211> LENGTH: 121
<212> TYPE: PRT
```

<213> ORGANISM: Artificial Sequence
<220> FEATURE:
<223> OTHER INFORMATION: VH of VAR2CSA binding domain

<400> SEQUENCE: 19

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Ser Pro Glu Arg Arg Leu Glu Trp Val
        35                  40                  45

Ala Glu Ile Ser Ile Thr Gly Arg Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Thr Arg Glu Gly Tyr Asp Tyr Ala Pro Ser Trp Phe Ala Tyr Trp Gly
            100                 105                 110

Gln Gly Thr Leu Val Thr Val Ser Ala
        115                 120

<210> SEQ ID NO 20
<211> LENGTH: 112
<212> TYPE: PRT
<213> ORGANISM: Artificial Sequence
<220> FEATURE:
<223> OTHER INFORMATION: VL of VAR2CSA binding domain

<400> SEQUENCE: 20

Asp Val Val Met Thr Gln Thr Pro Leu Ser Leu Pro Val Ser Leu Gly
1               5                   10                  15

Asp Gln Ala Ser Ile Ser Cys Arg Ser Gly Gln Thr Leu Val His Arg
            20                  25                  30

Asn Gly Ile Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Arg Thr Phe Gly Gly Gly Thr Lys Leu Glu Ile Lys
            100                 105                 110

<210> SEQ ID NO 21
<211> LENGTH: 363
<212> TYPE: DNA
<213> ORGANISM: Artificial Sequence
<220> FEATURE:
<223> OTHER INFORMATION: VH of VAR2CSA binding domain

<400> SEQUENCE: 21
gaggtgaagc tggtggagtc tgggggaggc ttagtgaagc ctggagggtc cctaaaactc      60
tcctgtgcag cctctggatt cactttcagt aactatgcca tgtcttgggt tcgccagtct     120
ccagagagga ggctggagtg ggtcgcagaa attagtatta ctggtcgtta cacctactat     180
ccagacactg tgacgggccg attcaccatc tccagagaca atgccaagaa caccctgtac     240

```
ctggaaatga gcagtctgag gtctgaggac acggccatgt attattgtac aagggaggga    300
tatgactacg ccccctcctg gtttgcttac tggggccaag ggactctggt cactgtctct    360
gca                                                                  363
```

<210> SEQ ID NO 22
<211> LENGTH: 336
<212> TYPE: DNA
<213> ORGANISM: Artificial Sequence
<220> FEATURE:
<223> OTHER INFORMATION: VL of VAR2CSA binding domain

<400> SEQUENCE: 22

```
gatgttgtga tgacccaaac tccactctcc ctgcctgtca gtcttggaga tcaagcctcc     60
atctcttgca gatctggtca gacccttgta catcgtaatg gaatcaccta tttagaatgg    120
tacctgcaga aaccaggcca gtctccaaag ctcctgatct acaaagtttc caaccgattt    180
tctggagtcc cagacaggtt cagtggcagt ggatcaggga cagatttcac actcaagatc    240
agcagagtgg aggctgagga tctgggaatt tattactgct ttcaaggttc acatgttcct    300
cggacgttcg gtggaggcac caagctggaa atcaaa                              336
```

<210> SEQ ID NO 23
<211> LENGTH: 14
<212> TYPE: PRT
<213> ORGANISM: Artificial Sequence
<220> FEATURE:
<223> OTHER INFORMATION: PNE-tag

<400> SEQUENCE: 23

Asn Tyr His Leu Glu Asn Glu Val Ala Arg Leu Lys Lys Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Myc-tag

<400> SEQUENCE: 24

Glu Gln Lys Leu Ile Ser Glu Glu Asp Leu
1               5                   10

<210> SEQ ID NO 25
<211> LENGTH: 4
<212> TYPE: PRT
<213> ORGANISM: Artificial Sequence
<220> FEATURE:
<223> OTHER INFORMATION: CaptureSelect C-tag

<400> SEQUENCE: 25

Glu Pro Glu Ala
1

<210> SEQ ID NO 26
<211> LENGTH: 8
<212> TYPE: PRT
<213> ORGANISM: Artificial Sequence
<220> FEATURE:
<223> OTHER INFORMATION: FLAG-tag

<400> SEQUENCE: 26

Asp Tyr Lys Asp Asp Asp Asp Lys
1               5

<210> SEQ ID NO 27
<211> LENGTH: 22
<212> TYPE: PRT
<213> ORGANISM: Artificial Sequence
<220> FEATURE:
<223> OTHER INFORMATION: 3xFLAG-tag

<400> SEQUENCE: 27

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 28
<211> LENGTH: 8
<212> TYPE: PRT
<213> ORGANISM: Artificial Sequence
<220> FEATURE:
<223> OTHER INFORMATION: Strep-tag

<400> SEQUENCE: 28

Trp Ser His Pro Gln Phe Glu Lys
1               5

<210> SEQ ID NO 29
<211> LENGTH: 6
<212> TYPE: PRT
<213> ORGANISM: Artificial Sequence
<220> FEATURE:
<223> OTHER INFORMATION: 6xHis-tag

<400> SEQUENCE: 29

His His His His His His
1               5

<210> SEQ ID NO 30
<211> LENGTH: 14
<212> TYPE: PRT
<213> ORGANISM: Artificial Sequence
<220> FEATURE:
<223> OTHER INFORMATION: V5-tag

<400> SEQUENCE: 30

Gly Lys Pro Ile Pro Asn Pro Leu Leu Gly Leu Asp Ser Thr
1               5                   10

<210> SEQ ID NO 31
<211> LENGTH: 15
<212> TYPE: PRT
<213> ORGANISM: Artificial Sequence
<220> FEATURE:
<223> OTHER INFORMATION: S-tag

<400> SEQUENCE: 31

Lys Glu Thr Ala Ala Ala Lys Phe Glu Arg Gln His Met Asp Ser
1               5                   10                  15

<210> SEQ ID NO 32
<211> LENGTH: 9
<212> TYPE: PRT
<213> ORGANISM: Artificial Sequence
<220> FEATURE:
<223> OTHER INFORMATION: HA-tag

<400> SEQUENCE: 32

Tyr Pro Tyr Asp Val Pro Asp Tyr Ala
1               5

<210> SEQ ID NO 33
<211> LENGTH: 11
<212> TYPE: PRT
<213> ORGANISM: Artificial Sequence
<220> FEATURE:
<223> OTHER INFORMATION: VSV-G-tag

<400> SEQUENCE: 33

Tyr Thr Asp Ile Glu Met Asn Arg Leu Gly Lys
1               5                   10

<210> SEQ ID NO 34
<211> LENGTH: 218
<212> TYPE: PRT
<213> ORGANISM: Artificial Sequence
<220> FEATURE:
<223> OTHER INFORMATION: GST-tag

<400> SEQUENCE: 34

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys
    210                 215

<210> SEQ ID NO 35
<211> LENGTH: 297
<212> TYPE: PRT
<213> ORGANISM: Artificial Sequence
<220> FEATURE:
<223> OTHER INFORMATION: HaloTag

<400> SEQUENCE: 35

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 36
<211> LENGTH: 864
<212> TYPE: PRT
<213> ORGANISM: Artificial Sequence
<220> FEATURE:
<223> OTHER INFORMATION: XTEN-tag

<400> SEQUENCE: 36

Ser Pro Ala Gly Ser Pro Thr Thr Glu Glu Gly Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
        35                  40                  45

```
Thr Ser Thr Glu Pro Ser Glu Gly Ser Ala Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Ser Glu Pro Ala Thr Ser Gly Ser Glu Thr Pro Gly Ser Pro Ala Gly
                100                 105                 110

Ser Pro Thr Ser Thr Glu Glu Gly Thr Ser Glu Ser Ala Thr Pro Glu
            115                 120                 125

Ser Gly Pro Gly Thr Ser Thr Glu Pro Ser Glu Gly Ser Ala Pro Gly
            130                 135                 140

Thr Ser Thr Glu Pro Ser Glu Gly Ser Ala Pro Gly Ser Pro Ala Gly
145                 150                 155                 160

Ser Pro Thr Ser Thr Glu Glu Gly Thr Ser Thr Glu Pro Ser Glu Gly
            165                 170                 175

Ser Ala Pro Gly Thr Ser Thr Glu Pro Ser Glu Gly Ser Ala Pro Gly
            180                 185                 190

Thr Ser Glu Ser Ala Thr Pro Glu Ser Gly Pro Gly Thr Ser Thr Glu
            195                 200                 205

Pro Ser Glu Gly Ser Ala Pro Gly Thr Ser Glu Ser Ala Thr Pro Glu
210                 215                 220

Ser Gly Pro Gly Ser Glu Pro Ala Thr Ser Gly Ser Glu Thr Pro Gly
225                 230                 235                 240

Thr Ser Thr Glu Pro Ser Glu Gly Ser Ala Pro Gly Thr Ser Thr Glu
                245                 250                 255

Pro Ser Glu Gly Ser Ala Pro Gly Thr Ser Glu Ser Ala Thr Pro Glu
                260                 265                 270

Ser Gly Pro Gly Thr Ser Glu Ser Ala Thr Pro Glu Ser Gly Pro Gly
            275                 280                 285

Ser Pro Ala Gly Ser Pro Thr Ser Thr Glu Glu Gly Thr Ser Glu Ser
290                 295                 300

Ala Thr Pro Glu Ser Gly Pro Gly Ser Glu Pro Ala Thr Ser Gly Ser
305                 310                 315                 320

Glu Thr Pro Gly Thr Ser Glu Ser Ala Thr Pro Glu Ser Gly Pro Gly
                325                 330                 335

Thr Ser Thr Glu Pro Ser Glu Gly Ser Ala Pro Gly Thr Ser Thr Glu
                340                 345                 350

Pro Ser Glu Gly Ser Ala Pro Gly Thr Ser Thr Glu Pro Ser Glu Gly
            355                 360                 365

Ser Ala Pro Gly Thr Ser Thr Glu Pro Ser Glu Gly Ser Ala Pro Gly
            370                 375                 380

Thr Ser Thr Glu Pro Ser Glu Gly Ser Ala Pro Gly Thr Ser Thr Glu
385                 390                 395                 400

Pro Ser Glu Gly Ser Ala Pro Gly Ser Pro Ala Gly Ser Pro Thr Ser
                405                 410                 415

Thr Glu Glu Gly Thr Ser Thr Glu Pro Ser Glu Gly Ser Ala Pro Gly
            420                 425                 430

Thr Ser Glu Ser Ala Thr Pro Glu Ser Gly Pro Gly Ser Glu Pro Ala
            435                 440                 445

Thr Ser Gly Ser Glu Thr Pro Gly Thr Ser Glu Ser Ala Thr Pro Glu
            450                 455                 460
```

```
Ser Gly Pro Gly Ser Glu Pro Ala Thr Ser Ser Glu Thr Pro Gly
465                 470                 475                 480

Thr Ser Glu Ser Ala Thr Pro Glu Ser Gly Pro Gly Thr Ser Thr Glu
                485                 490                 495

Pro Ser Glu Gly Ser Ala Pro Gly Thr Ser Glu Ser Ala Thr Pro Glu
                500                 505                 510

Ser Gly Pro Gly Ser Pro Ala Gly Ser Pro Thr Ser Thr Glu Glu Gly
                515                 520                 525

Ser Pro Ala Gly Ser Pro Thr Ser Thr Glu Glu Gly Ser Pro Ala Gly
530                 535                 540

Ser Pro Thr Ser Thr Glu Glu Gly Thr Ser Glu Ser Ala Thr Pro Glu
545                 550                 555                 560

Ser Gly Pro Gly Thr Ser Thr Glu Pro Ser Glu Gly Ser Ala Pro Gly
                565                 570                 575

Thr Ser Glu Ser Ala Thr Pro Glu Ser Gly Pro Gly Ser Glu Pro Ala
                580                 585                 590

Thr Ser Gly Ser Glu Thr Pro Gly Thr Ser Glu Ser Ala Thr Pro Glu
                595                 600                 605

Ser Gly Pro Gly Ser Glu Pro Ala Thr Ser Gly Ser Glu Thr Pro Gly
                610                 615                 620

Thr Ser Glu Ser Ala Thr Pro Glu Ser Gly Pro Gly Thr Ser Thr Glu
625                 630                 635                 640

Pro Ser Glu Gly Ser Ala Pro Gly Ser Pro Ala Gly Ser Pro Thr Ser
                645                 650                 655

Thr Glu Glu Gly Thr Ser Glu Ser Ala Thr Pro Glu Ser Gly Pro Gly
                660                 665                 670

Ser Glu Pro Ala Thr Ser Gly Ser Glu Thr Pro Gly Thr Ser Glu Ser
                675                 680                 685

Ala Thr Pro Glu Ser Gly Pro Gly Ser Pro Ala Gly Ser Pro Thr Ser
                690                 695                 700

Thr Glu Glu Gly Ser Pro Ala Gly Ser Pro Thr Ser Thr Glu Glu Gly
705                 710                 715                 720

Thr Ser Thr Glu Pro Ser Glu Gly Ser Ala Pro Gly Thr Ser Glu Ser
                725                 730                 735

Ala Thr Pro Glu Ser Gly Pro Gly Thr Ser Glu Ser Ala Thr Pro Glu
                740                 745                 750

Ser Gly Pro Gly Thr Ser Glu Ser Ala Thr Pro Glu Ser Gly Pro Gly
                755                 760                 765

Ser Glu Pro Ala Thr Ser Gly Ser Glu Thr Pro Gly Ser Glu Pro Ala
                770                 775                 780

Thr Ser Gly Ser Glu Thr Pro Gly Ser Pro Ala Gly Ser Pro Thr Ser
785                 790                 795                 800

Thr Glu Glu Gly Thr Ser Thr Glu Pro Ser Glu Gly Ser Ala Pro Gly
                805                 810                 815

Thr Ser Thr Glu Pro Ser Glu Gly Ser Ala Pro Gly Ser Glu Pro Ala
                820                 825                 830

Thr Ser Gly Ser Glu Thr Pro Gly Thr Ser Glu Ser Ala Thr Pro Glu
                835                 840                 845

Ser Gly Pro Gly Thr Ser Thr Glu Pro Ser Glu Gly Ser Ala Pro Gly
                850                 855                 860
```

<210> SEQ ID NO 37
<211> LENGTH: 314
<212> TYPE: PRT
<213> ORGANISM: Artificial Sequence
<220> FEATURE:
<223> OTHER INFORMATION: huEGFRt-tag

<400> SEQUENCE: 37

```
Asn Ile Lys His Phe Lys Asn Cys Thr Ser Ile Ser Gly Asp Leu His
1               5                   10                  15

Ile Leu Pro Val Ala Phe Arg Gly Asp Ser Phe Thr His Thr Pro Pro
            20                  25                  30

Leu Asp Pro Gln Glu Leu Asp Ile Leu Lys Thr Val Lys Glu Ile Thr
        35                  40                  45

Gly Phe Leu Leu Ile Gln Ala Trp Pro Glu Asn Arg Thr Asp Leu His
    50                  55                  60

Ala Phe Glu Asn Leu Glu Ile Ile Arg Gly Arg Thr Lys Gln His Gly
65                  70                  75                  80

Gln Phe Ser Leu Ala Val Val Ser Leu Asn Ile Thr Ser Leu Gly Leu
                85                  90                  95

Arg Ser Leu Lys Glu Ile Ser Asp Gly Asp Val Ile Ile Ser Gly Asn
            100                 105                 110

Lys Asn Leu Cys Tyr Ala Asn Thr Ile Asn Trp Lys Lys Leu Phe Gly
        115                 120                 125

Thr Ser Gly Gln Lys Thr Lys Ile Ile Ser Asn Arg Gly Glu Asn Ser
    130                 135                 140

Cys Lys Ala Thr Gly Gln Val Cys His Ala Leu Cys Ser Pro Glu Gly
145                 150                 155                 160

Cys Trp Gly Pro Glu Pro Arg Asp Cys Val Ser Cys Arg Asn Val Ser
                165                 170                 175

Arg Gly Arg Glu Cys Val Asp Lys Cys Asn Leu Leu Glu Gly Glu Pro
            180                 185                 190

Arg Glu Phe Val Glu Asn Ser Glu Cys Ile Gln Cys His Pro Glu Cys
        195                 200                 205

Leu Pro Gln Ala Met Asn Ile Thr Cys Thr Gly Arg Gly Pro Asp Asn
    210                 215                 220

Cys Ile Gln Cys Ala His Tyr Ile Asp Gly Pro His Cys Val Lys Thr
225                 230                 235                 240

Cys Pro Ala Gly Val Met Gly Glu Asn Asn Thr Leu Val Trp Lys Tyr
                245                 250                 255

Ala Asp Ala Gly His Val Cys His Leu Cys His Pro Asn Cys Thr Tyr
            260                 265                 270

Gly Cys Thr Gly Pro Gly Leu Glu Gly Cys Pro Thr Asn Gly Pro Lys
        275                 280                 285

Ile Pro Ser Ile Ala Thr Gly Met Val Gly Ala Leu Leu Leu Leu Leu
    290                 295                 300

Val Val Ala Leu Gly Ile Gly Leu Phe Met
305                 310
```